US012721745B2

(12) United States Patent
Cliff et al.

(10) Patent No.: US 12,721,745 B2
(45) Date of Patent: Sep. 1, 2026

(54) INTRAORAL APPLIANCE AND METHOD OF MANUFACTURING AN INTRAORAL APPLIANCE

(71) Applicant: Asesso Health Inc., Pleasanton, CA (US)

(72) Inventors: William C. Cliff, Pleasanton, CA (US); Abhijit Limaye, San Jose, CA (US)

(73) Assignee: ASESSO HEALTH INC., Pleasanton, CA (US)

( * ) Notice: Subject to any disclaimer, the term of this patent is extended or adjusted under 35 U.S.C. 154(b) by 0 days.

(21) Appl. No.: 19/432,479

(22) Filed: Dec. 24, 2025

(65) Prior Publication Data

US 2026/0183138 A1 Jul. 2, 2026

Related U.S. Application Data

(60) Provisional application No. 63/740,174, filed on Dec. 30, 2024.

(51) Int. Cl.
*A61F 5/56* (2006.01)

(52) U.S. Cl.
CPC ........ *A61F 5/566* (2013.01); *A61F 2005/563* (2013.01)

(58) Field of Classification Search
CPC ...... A61F 5/56; A61F 5/566; A61F 2005/563; A61C 5/90; A61C 7/08; A62B 9/06; A63B 71/085; A63B 2071/086; A63B 2071/088; A61M 16/0488; A61M 2016/049; A61M 2016/0493; A61M 2016/0495
See application file for complete search history.

(56) References Cited

U.S. PATENT DOCUMENTS

| | | | |
|---|---|---|---|
| 641,478 A | 1/1900 | Torres | |
| 869,658 A | 10/1907 | Sayre | |
| 1,002,112 A | 8/1911 | Allfree | |
| 5,865,619 A * | 2/1999 | Cross, III | A63B 71/085 433/6 |
| 6,415,794 B1 | 7/2002 | Kittelsen et al. | |
| 6,491,036 B2 | 12/2002 | Cook | |
| 6,539,943 B1 | 4/2003 | Kittelsen et al. | |
| 6,553,996 B2 | 4/2003 | Kittelsen et al. | |
| 6,619,290 B1 * | 9/2003 | Zacco | A61F 5/566 128/862 |

(Continued)

OTHER PUBLICATIONS

Crout, Danny K. et al., "Anatomy of an occlusal splint", Academy of General Dentistry; Mar.-Apr. 2017; https://www.agd.org/docs/default-source/self-instruction-(gendent)/gendent_ma17_crout.pdf; 8 pages.

*Primary Examiner* — Kari K Rodriquez
(74) *Attorney, Agent, or Firm* — LOZA & LOZA, LLP

(57) ABSTRACT

An intraoral appliance is disclosed herein. In an example, an intraoral appliance includes a left cap, a right cap, and a body connected to the left cap and to the right cap. In the example, the left and right caps include a bite plate having an upper surface and a lower surface, an inner sidewall extending from the lower surface, and an outer sidewall extending from the lower surface, wherein the inner sidewall and the outer sidewall form teeth receiving channels, and the body includes a left cap casing, a right cap casing, and a front band between the left cap casing and the right cap casing.

13 Claims, 24 Drawing Sheets

(56) References Cited

U.S. PATENT DOCUMENTS

| | | | | |
|---|---|---|---|---|
| 6,626,180 | B1 * | 9/2003 | Kittelsen | A63B 71/085 128/862 |
| 6,675,806 | B2 * | 1/2004 | Kittelsen | A63B 71/085 128/859 |
| 6,691,710 | B2 * | 2/2004 | Kittelsen | A63B 71/085 128/859 |
| 6,820,623 | B2 | 11/2004 | Cook | |
| 8,074,658 | B2 | 12/2011 | Kittelsen et al. | |
| 8,113,206 | B2 | 2/2012 | Roettger et al. | |
| 8,567,408 | B2 * | 10/2013 | Roettger | A61C 5/90 128/861 |
| 10,085,821 | B2 * | 10/2018 | Frey | A61F 5/566 |
| 10,342,694 | B1 | 7/2019 | Mowell et al. | |
| 11,311,407 | B1 * | 4/2022 | Fallon | A61F 5/566 |
| 12,011,386 | B1 | 6/2024 | Disessa et al. | |
| 12,016,792 | B2 | 6/2024 | Chodorow | |
| 2011/0017221 | A1 | 1/2011 | Garner et al. | |
| 2013/0239978 | A1 | 9/2013 | Stubbs et al. | |
| 2014/0026896 | A1 | 1/2014 | Roettger et al. | |
| 2015/0272773 | A1 | 10/2015 | Rico et al. | |
| 2016/0106521 | A1 | 4/2016 | Tanugula et al. | |
| 2016/0199215 | A1 | 7/2016 | Kopelman | |
| 2018/0078343 | A1 | 3/2018 | Falkel | |
| 2018/0344511 | A1 | 12/2018 | Brown | |
| 2019/0117442 | A1 | 4/2019 | Chodorow | |
| 2020/0000625 | A1 | 1/2020 | Robichaud et al. | |
| 2020/0261256 | A1 | 8/2020 | Simonetti | |
| 2020/0323678 | A1 | 10/2020 | Fallon et al. | |
| 2020/0345536 | A1 | 11/2020 | Letizia et al. | |
| 2020/0375790 | A1 | 12/2020 | Magness | |
| 2020/0376769 | A1 | 12/2020 | Murphy et al. | |
| 2022/0008243 | A1 | 1/2022 | Osorio Martini et al. | |
| 2022/0008244 | A1 | 1/2022 | Hart et al. | |
| 2022/0087854 | A1 | 3/2022 | Knutzen et al. | |
| 2022/0117777 | A1 | 4/2022 | Lasry et al. | |
| 2022/0370654 | A1 | 11/2022 | Ting et al. | |
| 2023/0000665 | A1 | 1/2023 | Ghuge | |
| 2023/0329897 | A1 | 10/2023 | Steiger | |
| 2023/0390103 | A1 | 12/2023 | Ghuge | |
| 2024/0156635 | A1 | 5/2024 | Maijer | |
| 2024/0358327 | A1 | 10/2024 | Kim et al. | |
| 2024/0366343 | A1 | 11/2024 | Kim et al. | |

* cited by examiner

Mold left and right caps — 2902

Position the left and right caps — 2904

Overmold a body around the left and right caps — 2906

INTRAORAL APPLIANCE AND METHOD OF MANUFACTURING AN INTRAORAL APPLIANCE

CROSS-REFERENCE TO RELATED APPLICATION

This application claims priority to provisional U.S. Patent Application Ser. No. 63/740,174, filed Dec. 30, 2025, which is incorporated by reference herein.

BACKGROUND

Temporomandibular Joint Dysfunction (TMD) and bruxism, often interconnected conditions, affect a significant portion of the population. TMD refers to dysfunction in the temporomandibular joint (TMJ) connecting the jaw to the skull, while bruxism involves the grinding or clenching of teeth, usually during sleep. TMD (sometimes referred to as TMJ) and/or bruxism can lead to various symptoms, including chronic headaches, muscle pain, damage to the teeth, and disrupted sleep patterns. The constant grinding of teeth associated with bruxism can exacerbate TMD symptoms, creating a cycle of discomfort and poor sleep. It is estimated that many millions of people suffer from TMD, with a notable percentage also experiencing bruxism, illustrating the widespread impact of these disorders on daily life and overall well-being.

SUMMARY

An intraoral appliance is disclosed herein. In an example, an intraoral appliance includes a left cap, a right cap, and a body connected to the left cap and to the right cap. In the example, the left cap includes a bite plate having an upper surface and a lower surface, an inner sidewall extending from the lower surface, and an outer sidewall extending from the lower surface, wherein the inner sidewall and the outer sidewall form a left-side teeth receiving channel, the right cap includes a bite plate having an upper surface and a lower surface, an inner sidewall extending from the lower surface, and an outer sidewall extending from the lower surface, wherein the inner sidewall and the outer sidewall form a right-side teeth receiving channel, and the body includes a left cap casing, a right cap casing, and a front band between the left cap casing and the right cap casing. In the example, the left cap is secured within the left cap casing with a front end of the bite plate nearer to the front band than a back end of the bite plate, and wherein the upper surface and the lower surface of the bite plate form a wedge that slopes downward from the front end of the bite plate to the back end of the bite plate, and the right cap is secured within the right cap casing with a front end of the bite plate nearer to the front band than a back end of the bite plate, and wherein the upper surface and the lower surface of the bite plate form a wedge that slopes downward from the front end of the bite plate to the back end of the bite plate.

In an example, an intraoral appliance as disclosed herein is produced in a process that involves molding the caps, positioning the caps, and then overmolding the body around the caps. In one example, a method of manufacturing an intraoral appliance involves placing a left cap in a first position, placing a right cap in a second position, which is opposite the left cap, and forming a body, which includes forming a left cap casing around the left cap, forming a right cap casing around the right cap, and forming a front band between the left cap casing and the right cap casing.

Other aspects in accordance with the invention will become apparent from the following detailed description, taken in conjunction with the accompanying drawings, illustrated by way of example of the principles of the invention.

BRIEF DESCRIPTION OF THE DRAWINGS

Throughout the description, similar reference numbers may be used to identify similar elements.

DETAILED DESCRIPTION

Figure 1:
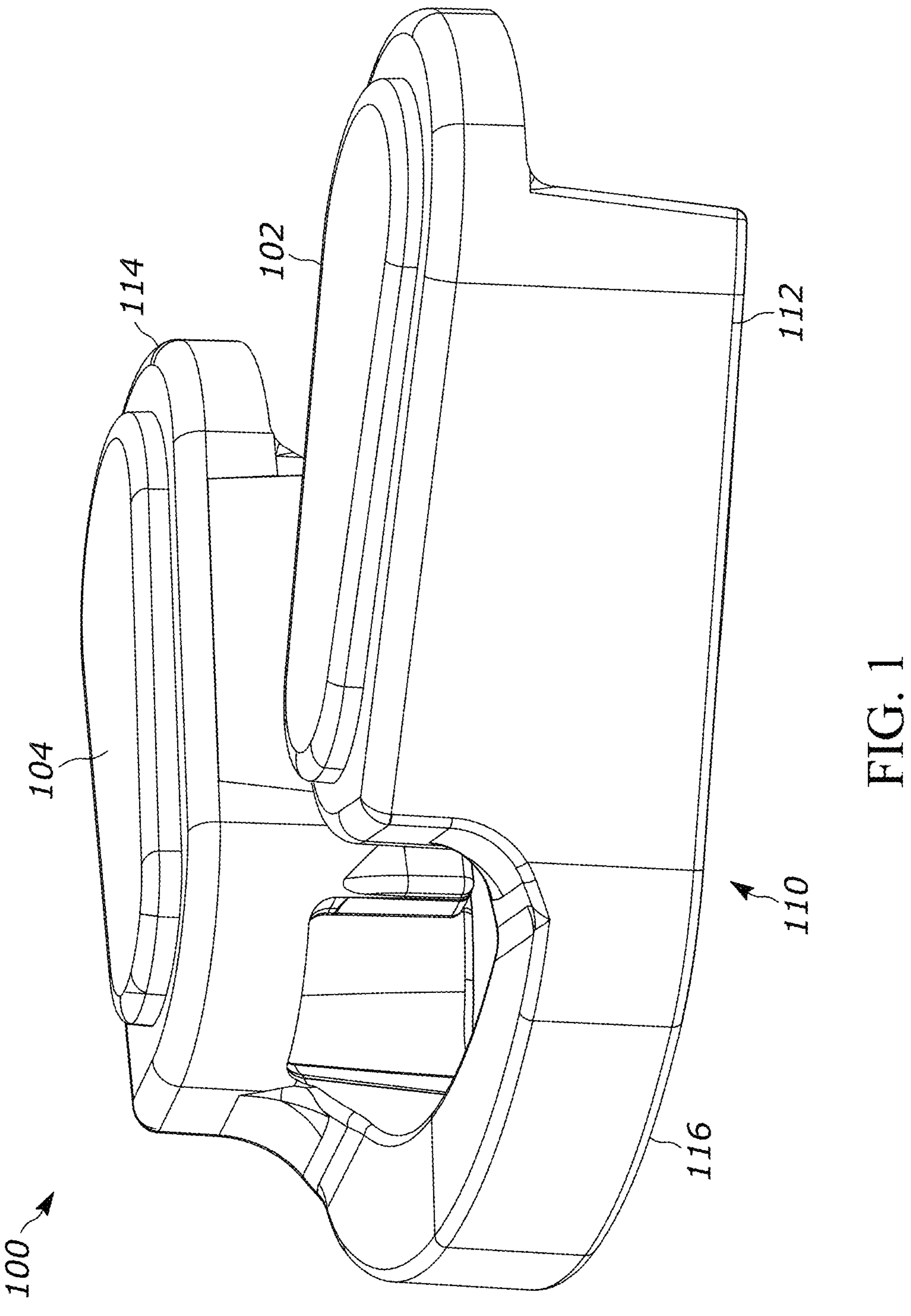
FIG. 1 is a perspective view of an example of an intraoral appliance that includes a left cap, a right cap, and a body.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment", "an embodiment", or similar language means that a particular feature, structure, or characteristic described in connection with the indicated embodiment is included in at least one embodiment of the present invention. Thus, the phrases "in one embodiment", "in an embodiment", and similar language throughout this specification may, but do not necessarily, all refer to the same embodiment.

As stated above, TMD and bruxism, often interconnected conditions, affect a significant portion of the population. TMD refers to dysfunction in the joint connecting the jaw to the skull, while bruxism involves the grinding or clenching of teeth, usually during sleep. TMD and/or bruxism can lead to various symptoms, including chronic headaches, muscle pain, damage to the teeth, and disrupted sleep patterns. The constant grinding of teeth associated with bruxism can exacerbate TMD symptoms, creating a cycle of discomfort and poor sleep. Treatments for bruxism and/or TMD may include stress management, dental interventions like dental splints or mouthguards, and lifestyle changes to reduce symptoms and prevent further damage to the teeth. Although dental splints or mouthguards are often used to address TMD and/or bruxism, dental splints and/or mouthguards are often uncomfortable to wear and/or are not effective in treating TMD and/or bruxism.

An intraoral appliance is disclosed herein. In an example, the intraoral appliance is designed to fit on a user's teeth (e.g., teeth of the lower jaw), with the goal of reducing, minimizing, or preventing teeth grinding, particularly while the user is sleeping. The intraoral appliance is comfortable to wear and specially designed to reduce, minimize, or prevent grinding of the teeth, e.g., TMD or bruxism. The intraoral appliance may also be referred to as, for example, a splint, a dental splint, an occlusal splint, or a mouthguard. Other terms may be used to refer to such an intraoral appliance. Some design criteria of the intraoral appliance disclosed herein include:

- Shape of the intraoral appliance;
- Hardness of the intraoral appliance, especially in the areas that are in direct contact with teeth, particularly the upper teeth;
- Fit of the intraoral appliance (e.g., a snug fit); and
- Comfort and ease of use of the intraoral appliance to increase compliance, which is the propensity of a user to consistently wear the intraoral appliance, e.g., each night while sleeping.

Shape—In an example, the shape of the intraoral appliance is designed to keep the mouth open between 7-10 mm (e.g., measured as the vertical distance (separation) between the upper and lower anterior teeth). Note, it has been observed that less than 7 mm of separation between the upper and lower anterior teeth or more than 10 mm of separation between the upper and lower anterior teeth may result in either discomfort or varying degrees of relief. It has also been observed that 7-10 mm of separation between the upper and lower anterior teeth provides the most optimal impact. That is, it has been found through observation and experimentation that an intraoral appliance that is designed to produce 7-10 mm of separation between the upper and lower anterior teeth provides the best results with respect to reducing, minimizing, or preventing teeth grinding, particularly while the user is sleeping. It is believed that the 7-10 mm separation distance between the upper and lower anterior teeth helps to keep the temporomandibular joint in a relaxed position, and thus inhibits the repetitive motion of the muscle that causes fatigue and hence pain. Although a separation distance of 7-10 mm has been found to be desirable, separation distances of between, for example, 6-11 mm, or 5-12 mm may also provide acceptable results, although a separation distance of 7-10 mm is preferred.

In an example, the intraoral appliance is designed with bite plates that have a small slope (e.g., an angle of approximately 3-6 degrees), which slopes downward from front to back. For example, bite plates of the intraoral appliance are thinner at a posterior end (e.g., nearer to the molars) and thicker at an anterior end (e.g., nearer to the anterior teeth). Once inserted between the teeth, the intraoral appliance forms a wedge that keeps the mouth somewhat open and the teeth separated. In an example, the thickness of the bite plates combined with the slope of the bite plates causes the teeth to maintain a 7-10 mm distance between the upper and lower anterior teeth, e.g., between the upper central incisors and the lower central incisors. In comparison with someone clenching their teeth, keeping the teeth open at 7-10 mm (e.g., measured as the vertical distance (separation) between the upper and lower anterior teeth) using an intraoral appliance with bite plates that have a slope (e.g., wedge shape), helps to reduce and or eliminate the urge to clench and helps to distribute pressure from pressure or clenching across the surface areas of the bite plates.

Hardness—In an example, at least a portion of the intraoral appliance (e.g., the bite plates) is made of either silicone or a thermoplastic elastomer material with a Shore A grade hardness between 75 and 95. A portion of the intraoral appliance is intentionally designed to be in this hardness grade so that it provides a tactile response to the teeth that there is a hard material between the teeth, which can reduce or prevent the urge to grind. It is believed that a softer material (less hardness) between the teeth promotes a chewing like activity (e.g., like a chewing gum) and will not help to reduce, minimize, or prevent grinding. In fact, many conventional dental splints or mouthguards are made of a soft material that may actually be exacerbating TMD or bruxism.

Fit—In an example, the intraoral appliance is designed to fit snugly over some of the posterior teeth, e.g., the premolars and the first molar. In an example, user-specific dimensions of the arrangement of the teeth in the oral cavity are captured using a custom smartphone application. The user-specific dimensions are then used to size the intraoral appliance to match the user-specific dimensions. In an example, internal surfaces of the intraoral appliance are designed with a snap-in feature that allows teeth receiving channels to flex slightly as necessary while the user is applying the intraoral appliance onto the teeth and then to hold on to the teeth snuggly and comfortably while worn within the mouth, e.g., within the oral cavity. In an example, the thickness of sidewalls of the caps of the intraoral appliance at their minimum dimension is designed at around 0.8 to 1 mm, such that the sidewalls have some flexibility. Removal of the intraoral appliance from the teeth is enhanced by flexibility of the sidewalls.

Comfort and long term compliance—Wearing an intraoral appliance can be discomforting and hence, in an example, the intraoral appliance is designed with only enough material to present a wedge between the teeth and to cover a minimum number of teeth to keep the desired separation distance between the teeth. As a result, in an example, the intraoral appliance does not cover the 2nd molar on both sides, reducing gag reflexes that users may have due overbearing material. Thus, in an example, the intraoral appliance is designed to cover as few teeth as possible, while still providing the desired separation and pressure distribution.

In an example, the front band of the intraoral appliance is designed to fit around the outside of the lower teeth (e.g., between the teeth and the lips), as opposed to against the inside of the lower teeth (e.g., between teeth and the tongue). This configuration of the front band helps to pull the intraoral appliance into place with anterior teeth helping to prevent movement while wearing the intraoral appliance.

In an example, side coverage of teeth by the intraoral device extends only on top of the 2 pre-molars and half of the 1st molar. In an example, the bite plate portion of the intraoral appliance extends and covers more than the first 2 pre-molars and half of the 1$^{st}$ molar to achieve a desired wedge shape.

In an example, the front band is designed to be thin to reduce its bulk so that the user's lips can close easily while sleeping and while keeping the teeth separated to the desired 7-10 mm. In an example, the front band has cross-sectional dimensions of between 4-7 mm in height and 1-2 mm in thickness, which can accommodate surface variations in the anterior teeth.

In an example, an intraoral appliance includes three separate components that are fused together into an integrated unitary appliance by overmolding. The three components include a left cap, a right cap, and a body. In an example, a fully assembled intraoral appliance includes the body overmolded over the left cap and the right cap. FIG. 1 is a perspective view of an example of an intraoral appliance 100 that includes a left cap 102, a right cap 104, and a body 110. The body of the intraoral appliance includes a left cap casing 112, a right cap casing 114, and a front band 116. Elements of the intraoral appliance are described below.

Figure 2:
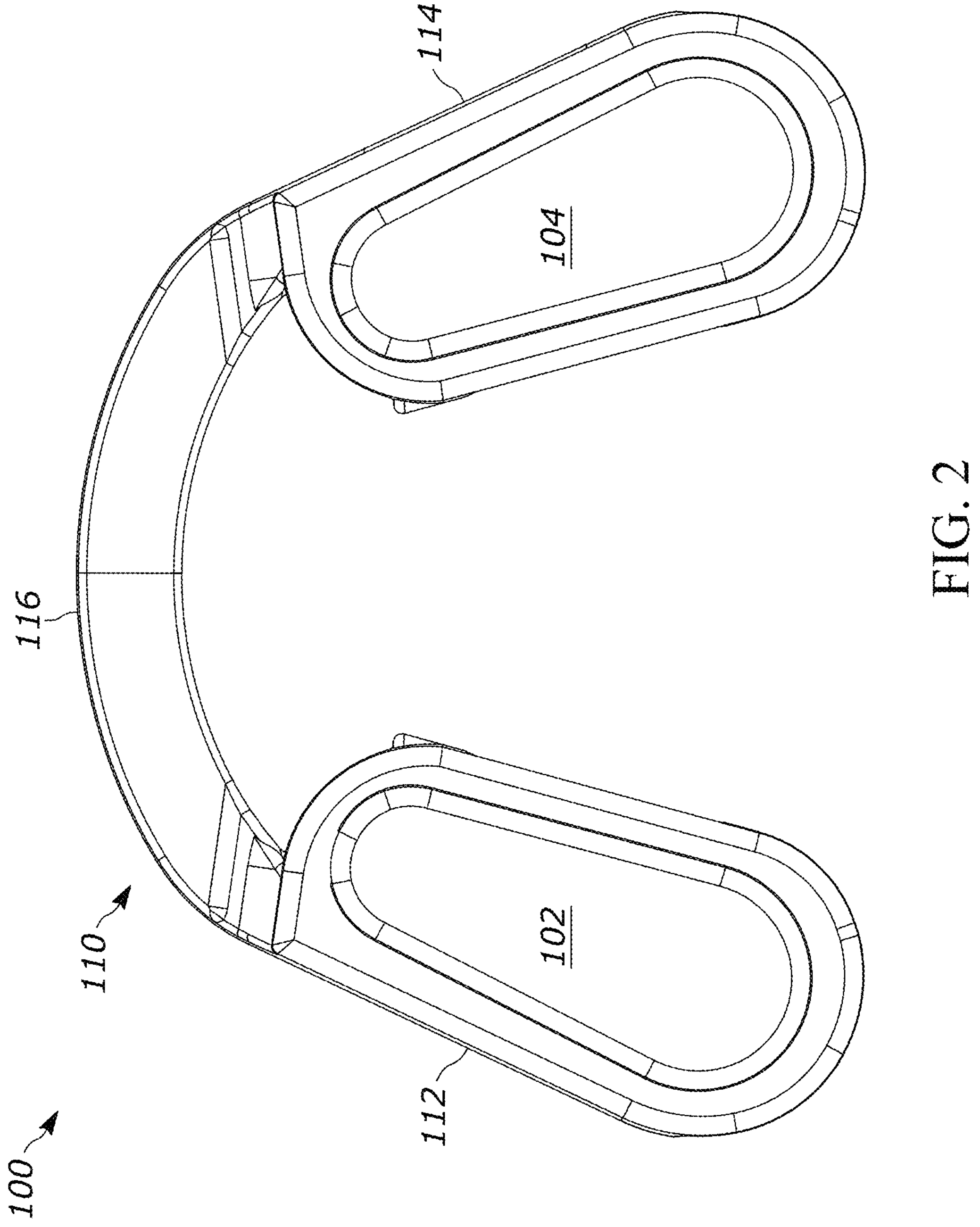
FIG. 2 is a top view of the intraoral appliance from FIG. 1.

FIG. 2 is a top view of the intraoral appliance 100 from FIG. 1. Components shown in the top view include a portion of the left cap 102, a portion of the left cap casing 112 of the body 110, a portion of the right cap 104, a portion of the right cap casing 114 of the body, and the front band 116 of the body. As used herein, the terms "left" and "right" are designated relative to a user that is wearing the intraoral appliance on the teeth as designed. Thus, with reference to the top view of FIG. 2, the left side of the intraoral device is on the left hand side of the figure and the right side of the intraoral device is on the right hand side of the figure. Additionally, the "front," "front end," or "front portion" of the appliance is at the top of the figure and the "back," "back end," or "back portion" of the appliance is at the bottom of the figure.

Figure 3:
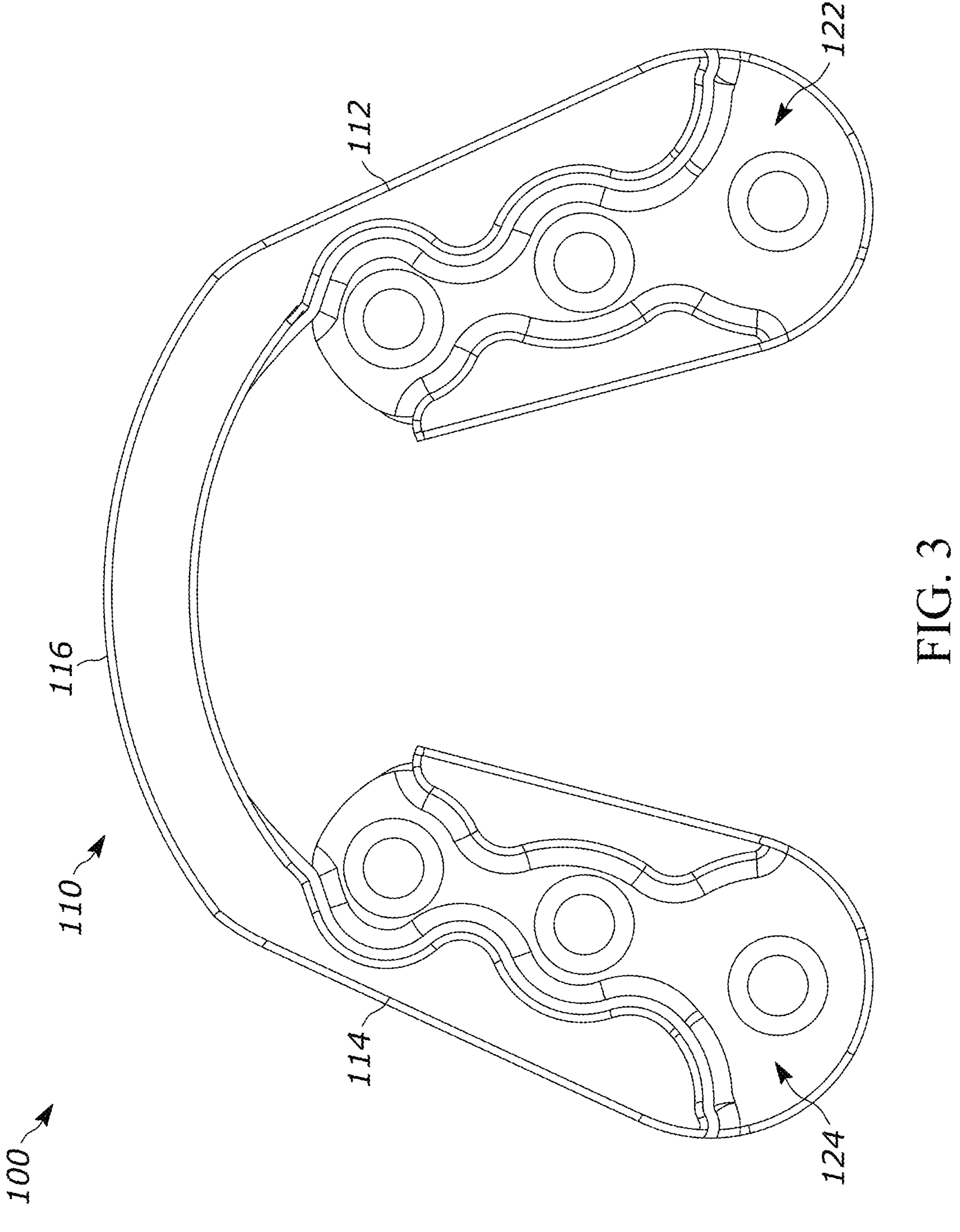
FIG. 3 is a bottom view of the intraoral appliance from FIGS. 1 and 2.

FIG. 3 is a bottom view of the intraoral appliance 100 from FIGS. 1 and 2. Components shown in the bottom view include a portion of the left cap casing 112 of the body 110, a portion of the right cap casing 114 of the body, and the front band 116 of the body. In the bottom view of FIG. 3, the left side of the appliance is on the right hand side of the figure and the right side of the appliance is on the left hand side of the figure, which is opposite to FIG. 2. Similar to FIG. 2, the "front," "front end," or "front portion" of the appliance is at the top of the figure and the "back," "back end," or "back portion" of the appliance is at the bottom of the figure. FIG. 3 shows a left-side receiving channel 122 and a right-side receiving channel 124 of the intraoral appliance as well as the front band. In the bottom view, the left cap and the right cap are not visible because the left cap and the right cap are covered by the body.

Figure 4:
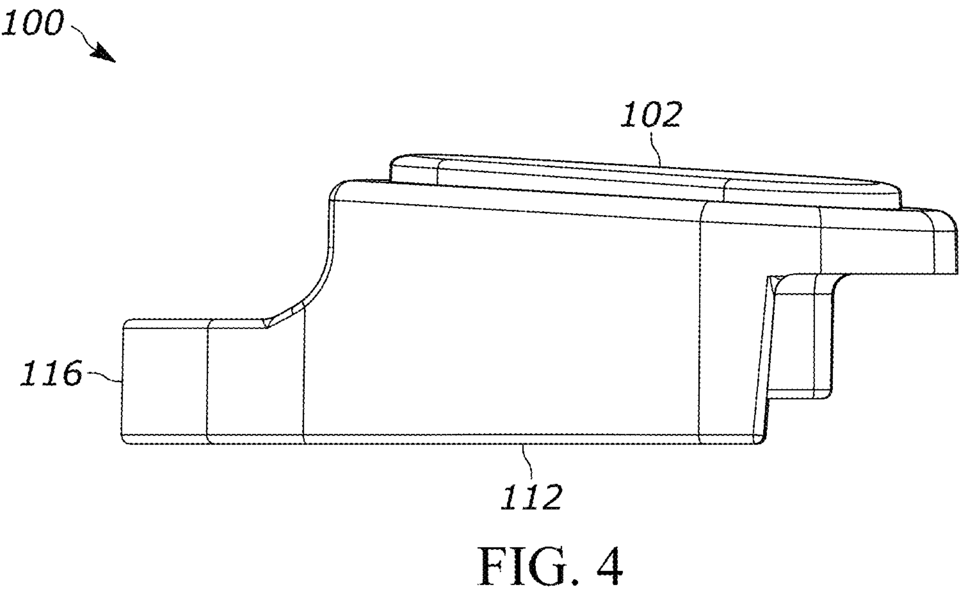
FIG. 4 is a perspective view of the left side of the intraoral appliance.

FIG. 4 is a perspective view of the left side of the intraoral appliance 100. The left side view shows a portion of the front band 116, a portion of the left side casing 112, and a portion of the left cap 102. As shown in FIG. 4, the left cap casing has a height dimension that is larger than the front band. FIG. 4 also shows that an upper surface of the left cap is exposed (e.g., not covered by the left cap casing) so that some of the upper teeth will contact directly with upper surface of the left cap.

Figure 5:
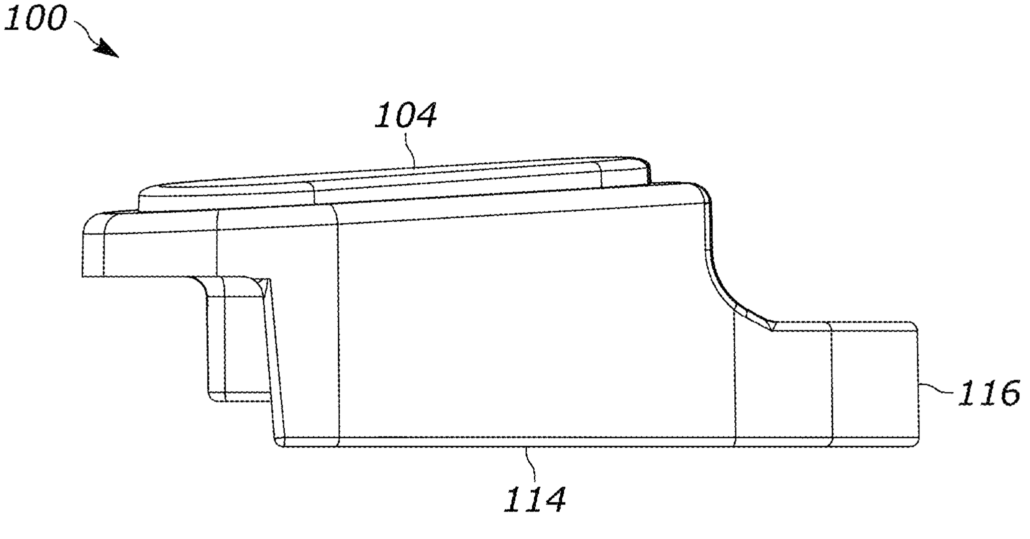
FIG. 5 is a perspective view of the right side of the intraoral appliance.

FIG. 5 is a perspective view of the right side of the intraoral appliance 100. The right side view shows a portion of the front band 116, a portion of the right cap casing 114, and a portion of the right cap 104. As shown in FIG. 5, the right cap casing has a height dimension that is larger than the front band. FIG. 5 also shows that an upper surface of the right cap is exposed (e.g., not covered by the right cap casing) so that some of the upper teeth will contact directly with upper surface of the right cap. Contact between the occlusal surfaces of the upper teeth with the hard upper surface of the left and right caps can prevent clenching and grinding.

Figure 6:
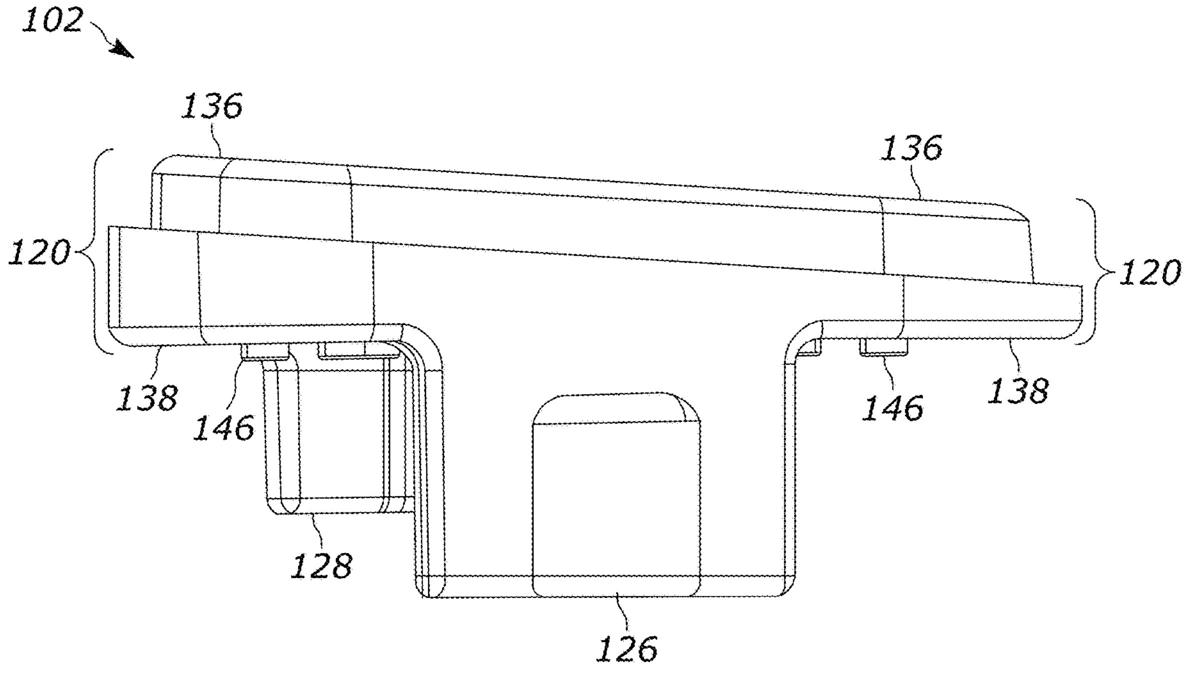
FIG. 6 is a perspective view of the left cap.

FIG. 6 is a perspective view of the left cap 102. The view of FIG. 6 is oriented in conjunction with the side view of FIG. 4. The left cap includes a bite plate 120, an outer sidewall 126 (in the foreground) extending from the bite plate, and an inner sidewall 128 (in the background) extending from the bite plate. With regard to an assembled intraoral appliance, the left side of the left cap as shown in FIG. 6 is the front end of the left cap and the right side of the left cap as shown in FIG. 6 is the back end of the left cap. The bite plate of the left cap has an upper surface 136 and a lower surface 138, which form a wedge that slopes downward from the front end to the back end of the left cap. In an example, the slope of the wedge is set at an angle that produces a separation between the anterior teeth of a person wearing the intraoral appliance of about 7-10 mm. The slope of the wedge is described below with reference to FIGS. 7A and 7B.

The left cap 102 may also include some other structural features, e.g., posts 146 and/or cavities, that help to secure the left cap to the body through overmolding. Although not shown, the right cap is similar to the left cap, with the inner sidewall and outer sidewall on opposite sides with respect to the left cap. For example, the left cap and the right cap are mirror images of each other.

In an example, it is desirable that the left cap and the right cap are made of a hard material, as it has been observed that direct contact between occlusal surfaces of the teeth and a hard material can inhibit the body's penchant to bite down. In contrast, it has been observed that a soft material in direct contact with the occlusal surfaces of the teeth can enhance/induce the body to bite down. Thus, in an example, the left and right caps are made from a material with a Shore A hardness of 75-95 in one example, or 70-90 in another example, or 70-95 in another example. In an example, the left and right caps are molded from a plastic material with a Shore A hardness of 75-95. An example of a material that can be used to form the left and right caps is ATEVA® 2829AG.

Because the caps are made of a hard material, the left and right sidewalls of the caps provide a stiffness to the teeth receiving channels of the intraoral appliance that enables the intraoral appliance to fit snuggly over the contacted teeth. For example, some conventional nightguards are made entirely of a thermoplastic material and a user is expected to heat the nightguard and then fit the nightguard over the teeth. While heated, the user needs to place the nightguard between their teeth for 2-3 minutes under pressure, which is typically provided by biting down on the nightguard. The vertical force applied to the nightguard by biting down can cause sidewalls of the nightguard to flare outwards, which can lead to a less than ideal fit once the nightguard cools and sets its form. In contrast, the sidewalls of the caps disclosed herein are made of a material that does not change shape when exposed to heating that is intended to soften the material of the body. In the design disclosed herein, the user is also requested to heat the intraoral appliance to allow the thermoplastic material of the body to form over the teeth but the resulting shape of the thermoplastic material of the body is influenced by the relatively hard caps, which have thermoset properties. As such, when the intraoral appliance is heated up as needed for custom fitting, the material of the body inside the teeth receiving channels (e.g., including the surfaces that are in contact with the bottom teeth) is allowed to form around the teeth, while the caps maintain their shape. In an example, the inner sidewall and outer sidewall of a cap applies force from both sides while the body is being formed around the teeth, which prevents side-flaring and helps the intraoral appliance to snugly fit over the teeth once the intraoral appliance cools down and its form is set.

In an example, the size of the front band of the intraoral appliance also adapts through the heating and fitting process. For example, while heated, the front band will stretch to fit snuggly across the lower front teeth and then the front band will fix its shape upon cooling down. In an example, the cross-sectional dimensions of the front band are selected to enable a desired range of adaptation (as a result of a heating and cooling process) that is expected for a typical range of humans. In an example, the front band has cross-sectional dimensions of 4-7 mm in height (e.g., wherein height is parallel to the length of a tooth) and 1-2 mm in thickness (e.g., where thickness is orthogonal to the front surface of a tooth), although other dimensions are possible.

In an example, the thermoplastic material of the body is chosen such that the body sets its form within about 60 seconds of cooling as opposed to 2-3 minutes of cooling, which can increase user comfort during a customization process. An example of a material that can be used for the body is MAKROLON® 2458.

An example of the desired slope of the bite plates is described with reference to FIGS. 7A and 7B.

Figure 7A:
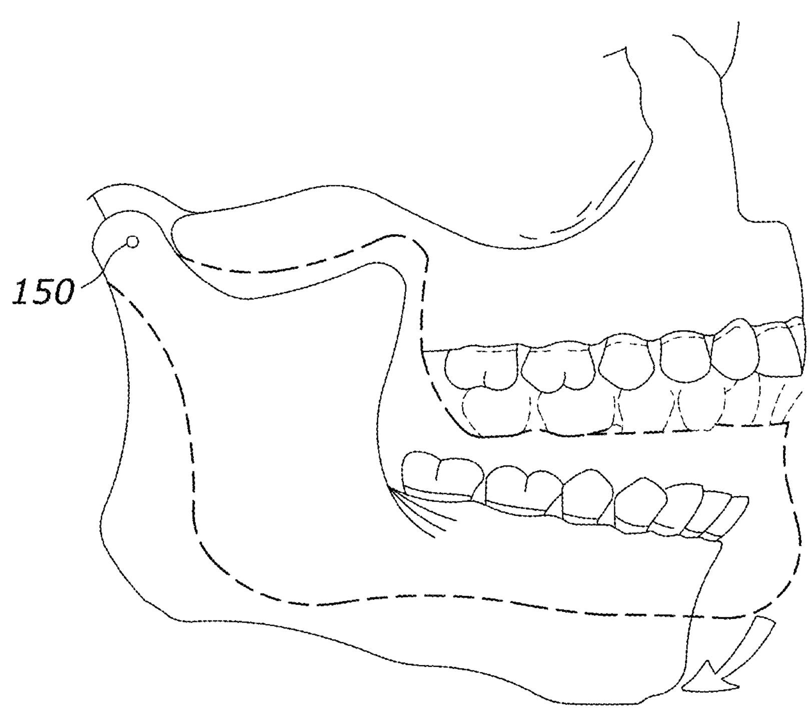
FIG. 7A shows the skeletal structure and teeth of a human with the jaw in a first position.
Figure 7B:
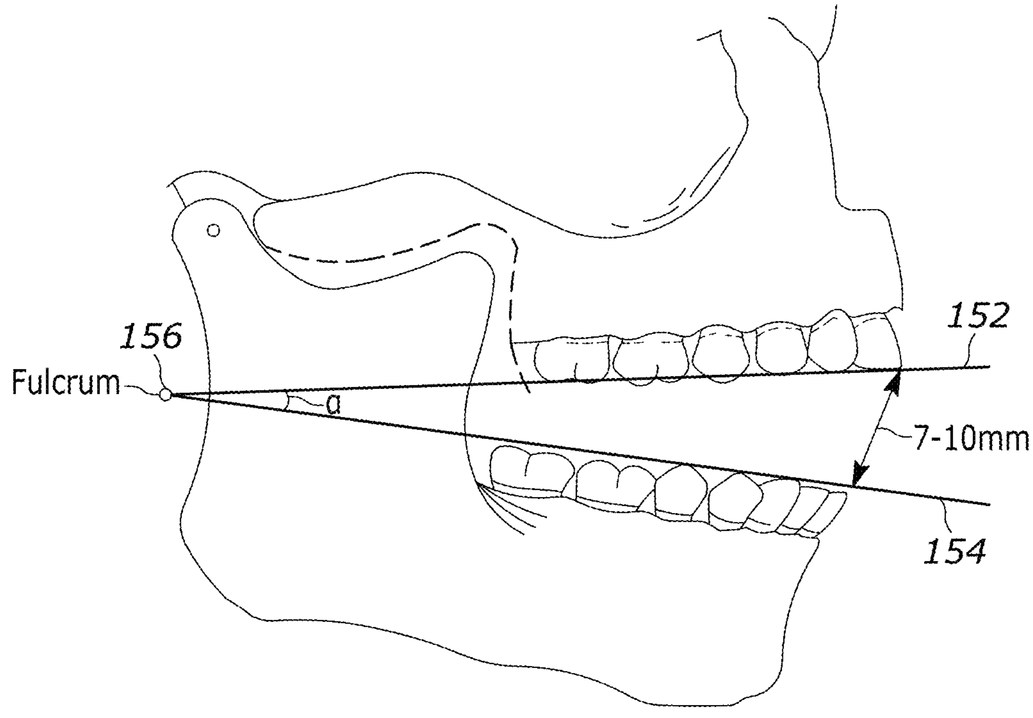
FIG. 7B shows only the first position from FIG. 7A along with a first line that runs parallel to the occlusal surfaces of the upper teeth and a second line that runs parallel to the occlusal surfaces of the lower teeth.

FIG. 7A shows the skeletal structure and teeth of a human with the jaw in a first position, e.g., an open position. FIG. 7A also illustrates, via overlaid dashed lines, the skeletal structure and teeth of the human with the jaw in a second position, e.g., a closed position. As is well known, the jaw is anchored by, and rotates around, the mandibular joint 150 (also known as the temporomandibular joint). FIG. 7B shows only the first position, e.g., the open position, from FIG. 7A along with a first line 152 that runs parallel to the occlusal surfaces of the upper teeth and a second line 154 that runs parallel to the occlusal surfaces of the lower teeth. As shown in FIG. 7B, the two lines intersect at a point 156 and form an angle, $\alpha$. In an example, the slope of the wedge formed by the upper surface and the lower surface of a cap (left or right) is set based on the angle, $\alpha$. For example, it is desirable that the slope of the wedge of the intraoral appliance matches the angle formed by the intersection of the two lines in FIG. 7B when the upper and lower anterior teeth are separated by about 7-10 mm. In an example, the angle, $\alpha$, to achieve separation of about 7-10 mm for a wide range of humans is in the range of 3-6 degrees. Thus, in an example, the slope of the wedge of the caps of the intraoral appliance is set to around 3-6 degrees, with the angle being measured from the intersection of a first line projecting from the upper surface of a cap and a second line projecting from the lower surface of the same cap. An example of the slope of a wedge formed by a cap is shown in FIG. 8.

Figure 8:
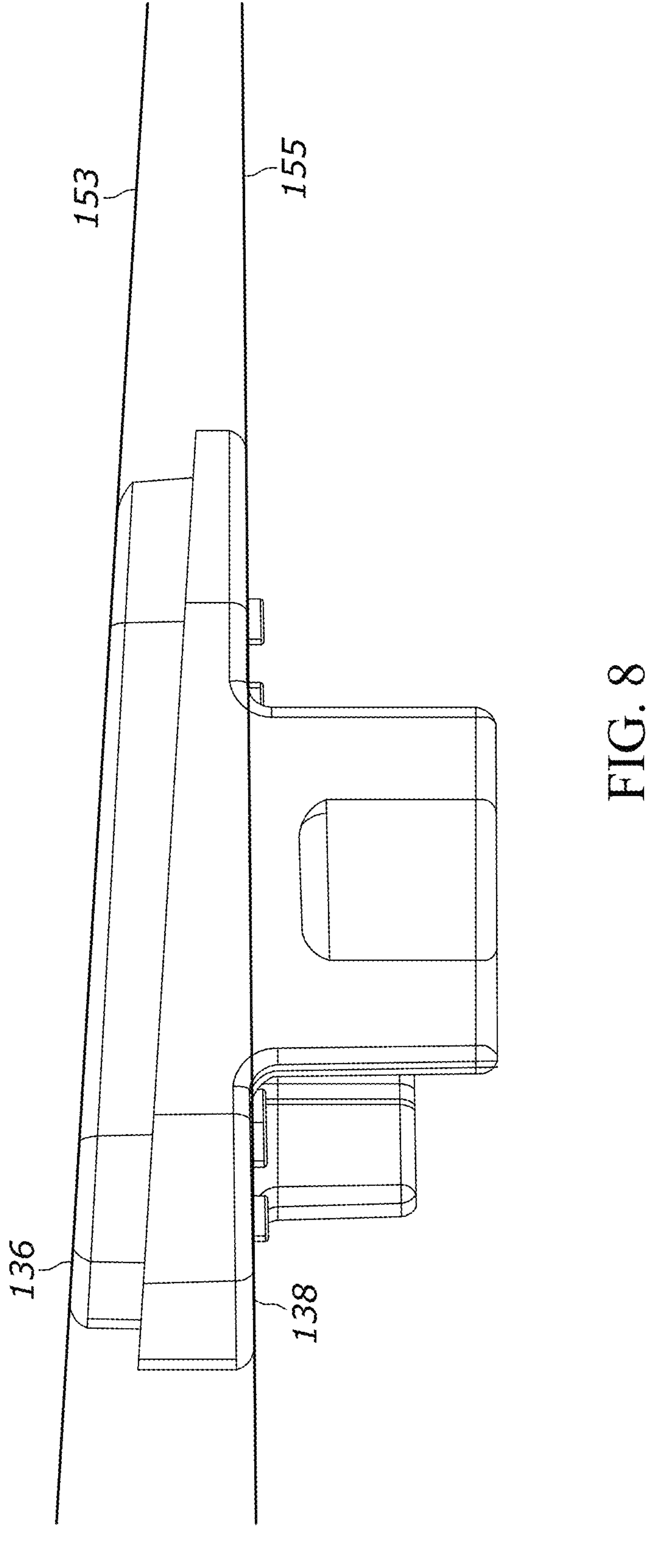
FIG. 8 illustrates a portion of a wedge formed by a first line projecting from the upper surface of the cap and a second line projecting from the lower surface of the same cap.

FIG. 8 illustrates a portion of a wedge formed by a first line 153 projecting from the upper surface 136 of the cap and a second line 155 projecting from the lower surface 138 of the same cap. The angle of the wedge would be measured relative to the point at which the two lines intersect. The point of intersection between the two lines is not shown in FIG. 8 but would be off to the right of the figure as the two lines extend further. In an example, the slope of the wedge of the caps of the intraoral appliance is set to be within a range of angles that will achieve about 7-10 mm of anterior teeth separation for humans, e.g., around 3-6 degrees as described above. In one example, the front end of the cap has a height dimension of 5 mm, the back end of the cap has a height dimension of 1.5 mm, and the length of the end cap is in the range of about 15-25 mm. Given such dimensions, the angle, $\alpha$, of the wedge is approximately in the range of 3-6 degrees. In one example, the front end of the cap has a height dimension of 5 mm, the back end of the cap has a height dimension of 1.5 mm, and the length of the end cap is about 25 mm, which corresponds to an angle, $\alpha$, of about 4.3 degrees. The angle of the wedge formed by the upper surface and the lower surface of the caps will help to set the angle between the upper surface of the caps and a surface of the body (after overmolding) that is in contact with occlusal surfaces of some of the bottom teeth.

Figure 9:
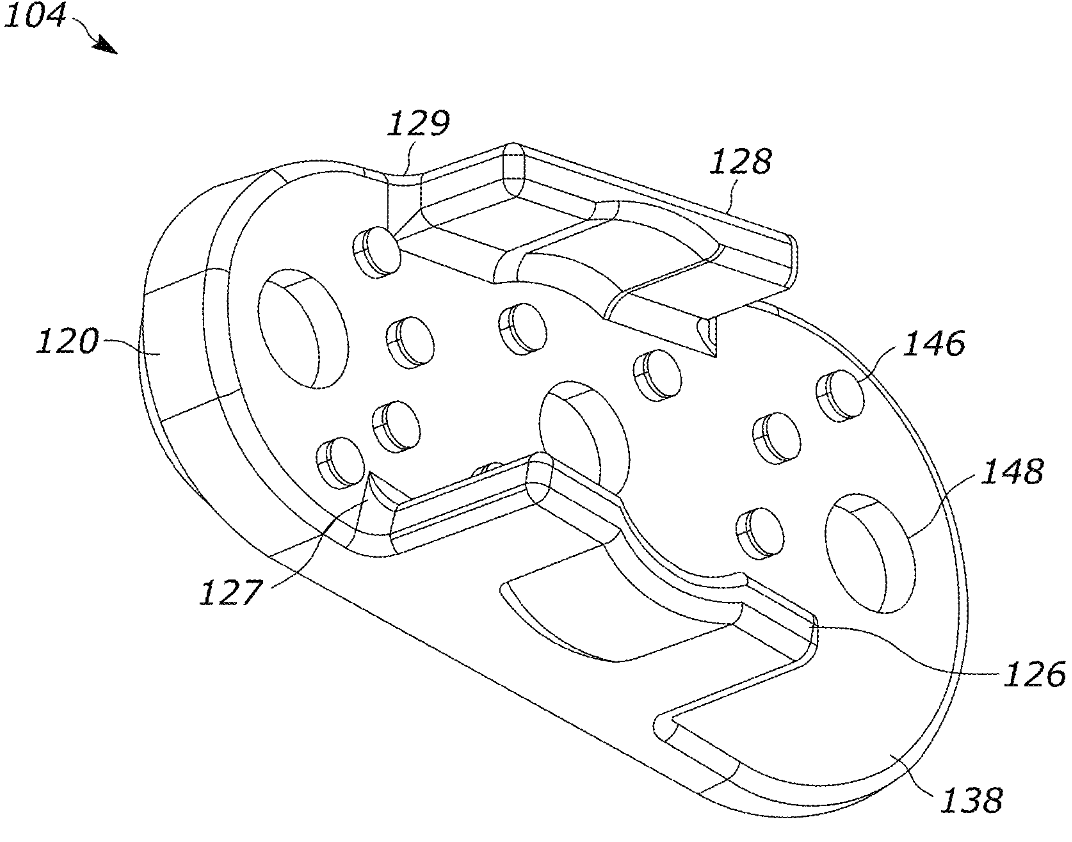
FIG. 9 shows a perspective view of the bottom of a right cap.

FIG. 9 shows a perspective view of the bottom of a right cap 104. The bottom perspective view shows the bottom surface 138, the outer sidewall 126, the inner sidewall 128, the front end, and the back end of the right cap. In the example, the outer sidewall has a larger depth dimension than the inner sidewall. It has been found that the two different depths of the sidewalls provide a good balance between comfort and secure fit, with the smaller depth of the inner sidewall enhancing comfort while the larger depth of the outer sidewall provides a more secure fit as it provides a larger surface area for applying lateral force against the adjacent teeth.

In an example, the right cap 104 shown in FIG. 9 includes a stiffening structure 129 at the intersection between the bite plate and the inner sidewall 128. For example, the stiffening structure includes additional material at the intersection between the lower surface 138 of the bite plate 120 and the inner sidewall that reduces flexion of the sidewall relative to the bite plate. Although only partially shown in FIG. 9, the cap may also include a stiffening structure 127 at the intersection between the lower surface 138 of the bite plate 120 and the outer sidewall 126. For example, the stiffening structure includes additional material at the intersection between the bite plate and the outer sidewall that reduces flexion of the sidewall relative to the bite plate. FIG. 9 also shows posts 146 and cavities 148 that may be present on the bottom surface 138 of the bite plate 120. Such structural features may be helpful in securing the cap to the body.

Figure 10:
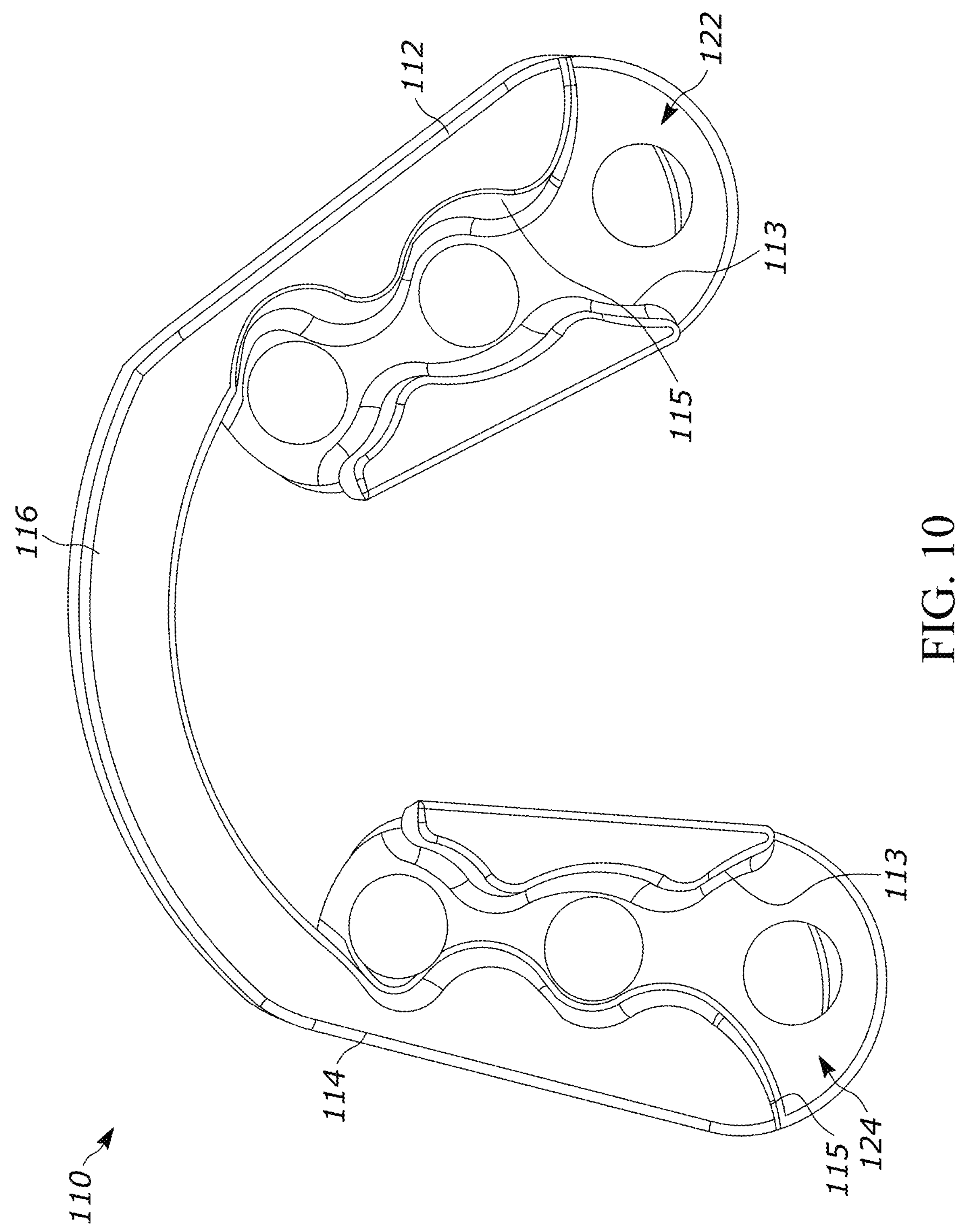
FIG. 10 is a perspective view of the bottom of the body without the caps secured within the cap casings.

FIG. 10 is a perspective view of the bottom of the body 110 without the caps secured within the cap casings. It should be noted that the body is typically not produced without being overmolded over the left and right caps, but is shown in FIG. 10 for description purposes. Components of the body visible in FIG. 10 include the front band 116, the left cap casing 112, and the right cap casing 114. Each cap casing includes an inner sidewall 113 and an outer sidewall 115 that form the left and right teeth receiving channels 122 and 124, respectively. In an example, the left and right teeth receiving channels are positioned and shaped to mate with two or three teeth, e.g., with two premolars and half of the first molar. In the example of FIG. 10, the openings 149 (e.g., circular openings) that extend entirely through the body are provided for ease of overmolding. In an example, the openings 149 in the body match the positions of the circular cavities 148 in the left and right caps, all of which are elements that relate to the overmolding process. For example, the openings correspond to elements that are used in the overmolding process to hold the left and right caps in place within a mold that helps to form the body.

Figure 11:
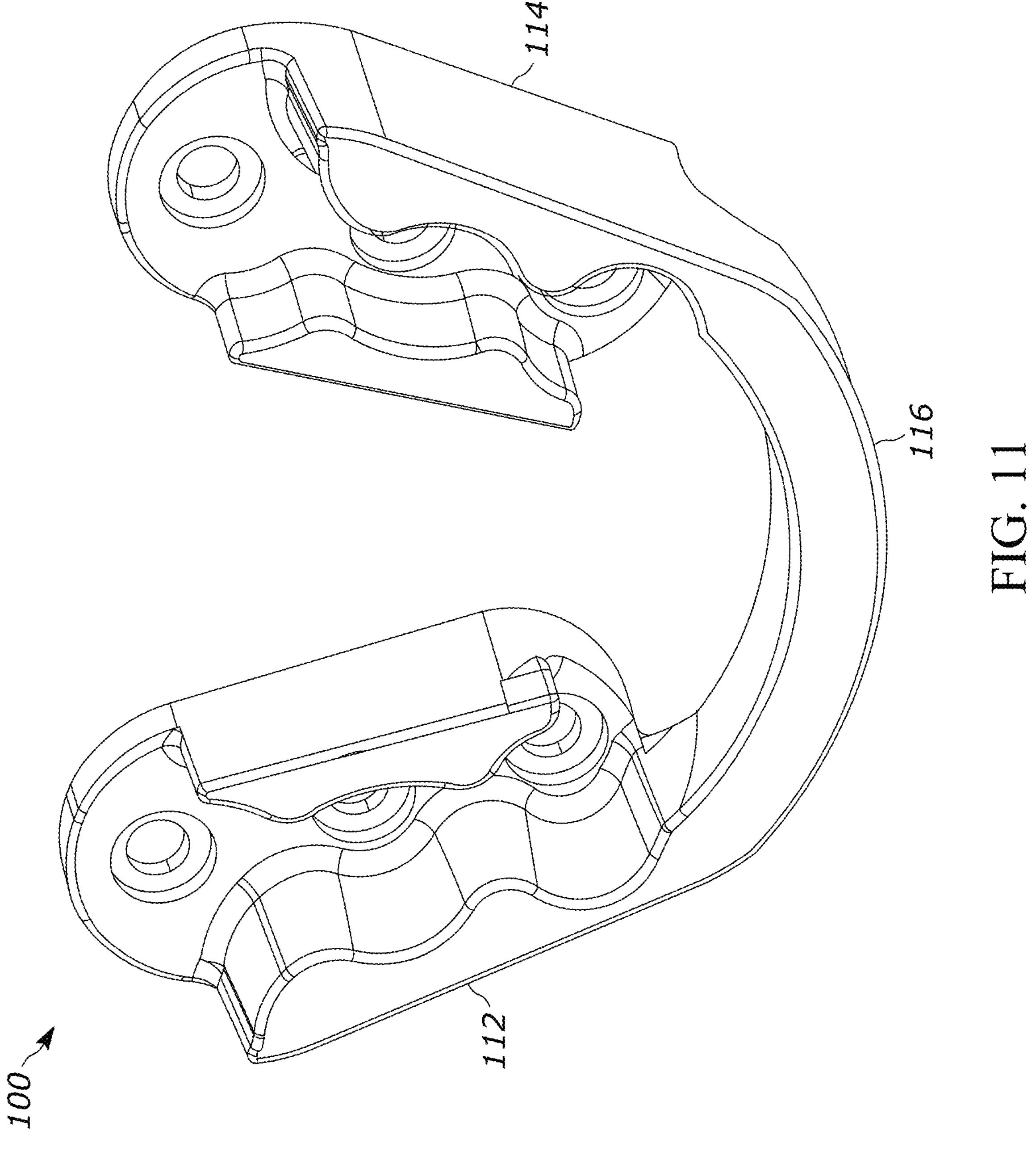
FIG. 11 is a perspective view of the bottom of the intraoral appliance.

FIG. 11 is a perspective view of the bottom of the intraoral appliance 100. FIG. 11 shows the front band 116, the left cap casing 112, and the right cap casing 114. In addition, FIG. 11 shows the left-side teeth receiving channel and the right-side teeth receiving channel.

Figure 12:
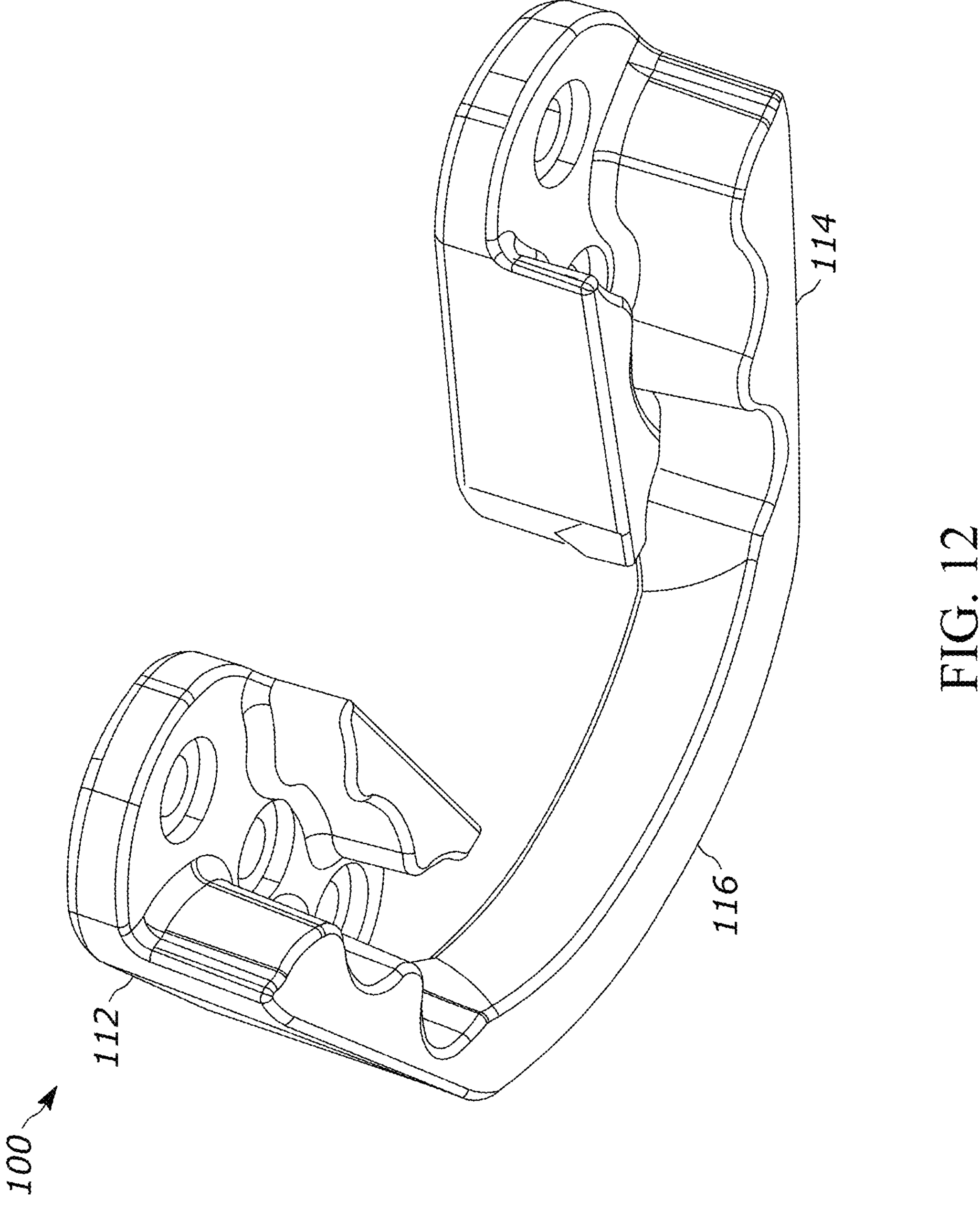
FIG. 12 is a perspective view of the bottom of the intraoral appliance.

FIG. 12 is a perspective view of the bottom of the intraoral appliance 100 that shows the front band 116, the left cap casing 112, and the right cap casing 114.

Figure 13A:
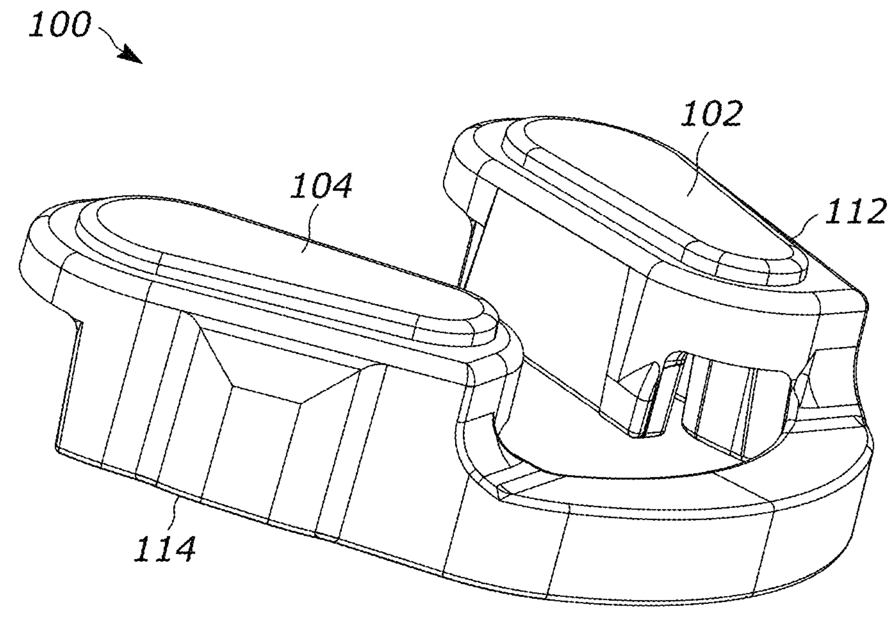
FIG. 13A is a perspective view of the intraoral appliance that shows the front band, the left cap casing, and the right cap casing.
Figure 13B:
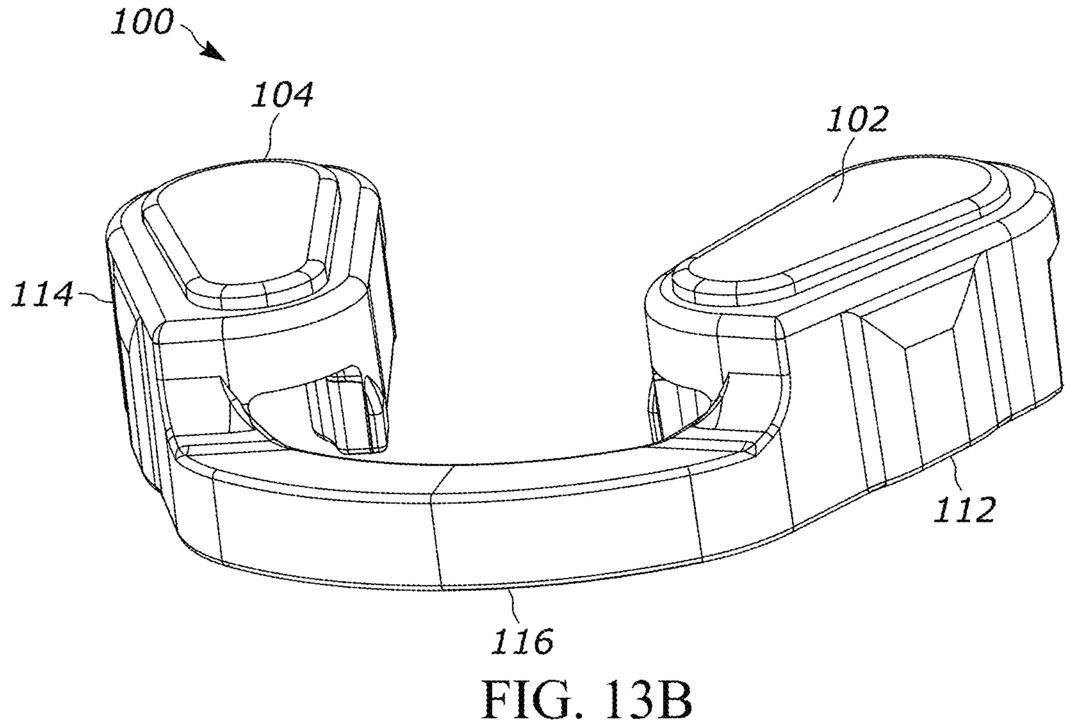
FIG. 13B is another perspective view of the intraoral appliance that shows the front band, the left cap casing, and the right cap casing.
Figure 13C:
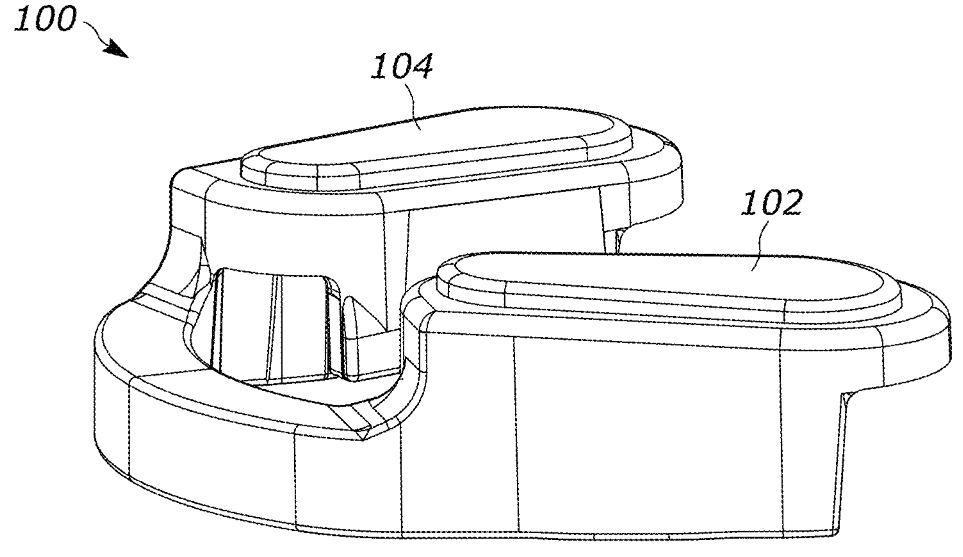
FIG. 13C is another perspective view of the intraoral appliance that shows the front band, the left cap casing, and the right cap casing.

FIGS. 13A, 13B, and 13C are perspective views of the intraoral appliance 100 that show the front band 116, the left cap casing 112, and the right cap casing 114. FIGS. 13A, 13B, and 13C also show an exposed portion of the upper surface of the left cap 102 and an exposed portion of the upper surface of the right cap 104. As described above (although not specifically shown in FIGS. 13A, 13B, and 13C), the upper surface of the bite plates of the caps and the surfaces of the cap casings that contact the occlusal surfaces of the lower teeth form a wedge that slopes downward from front to back, e.g., from the front end of the caps to the back end of the caps.

Figure 14:
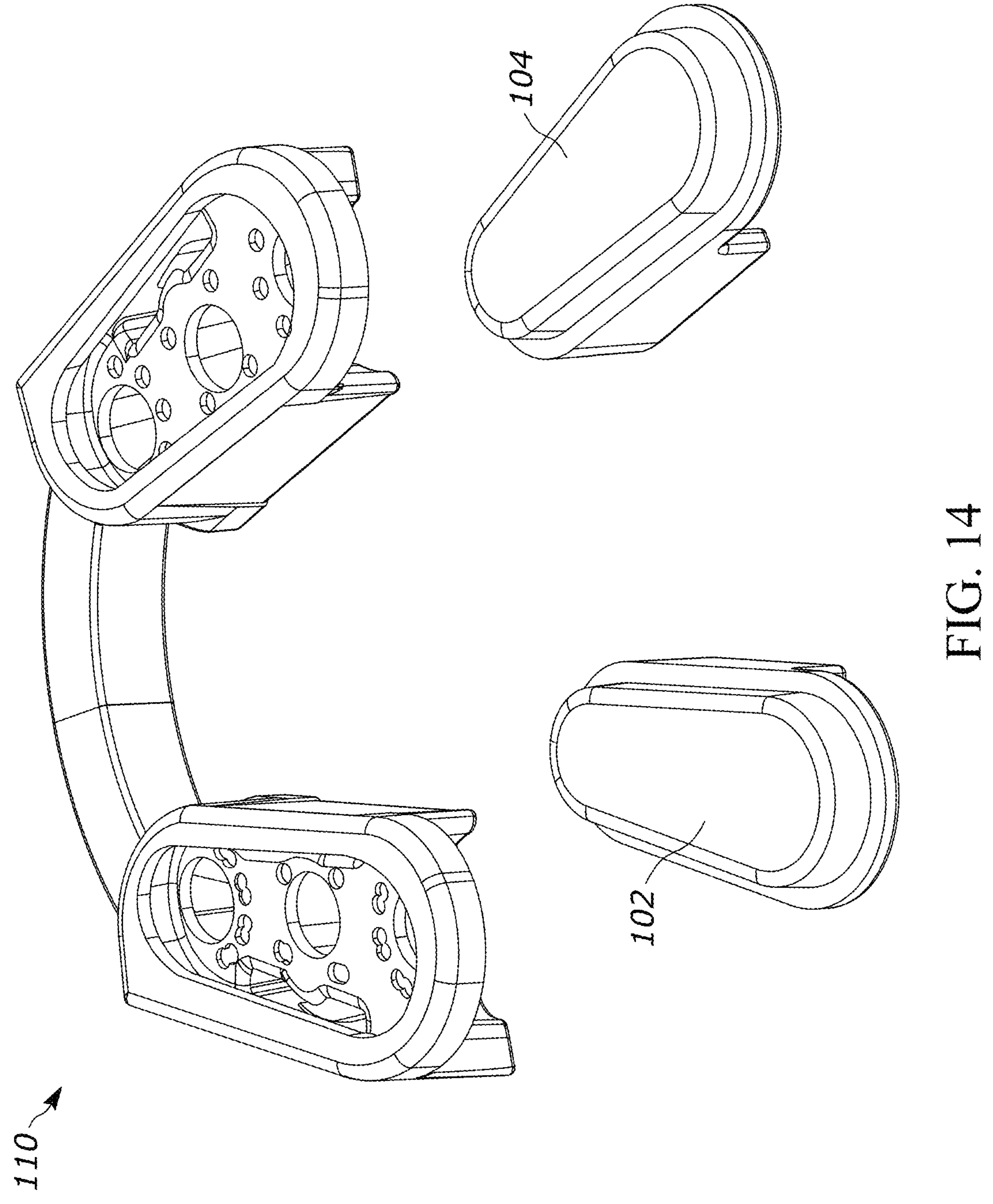
FIG. 14 shows a perspective view of the body disassociated from the left cap and from the right cap.

FIG. 14 shows a perspective view of the body 110 disassociated from the left cap 102 and from the right cap 104. As shown in FIG. 14, it can be understood how the caps are secured in the left and right cap casings of the body upon overmolding.

Figure 15:
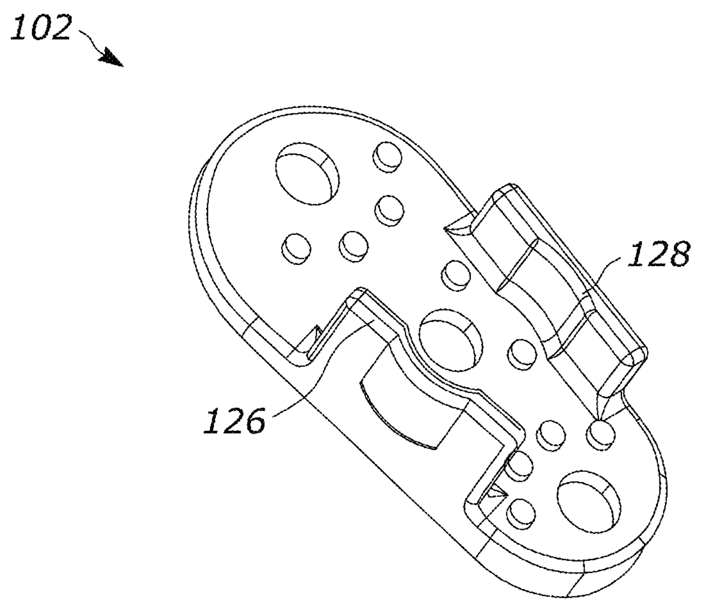
FIG. 15 is a perspective view of the bottom of the left cap.

FIG. 15 is a perspective view of the bottom of the left cap 102. In the example, the outer sidewall 126 has a larger depth dimension than the inner sidewall 128.

Figure 16:
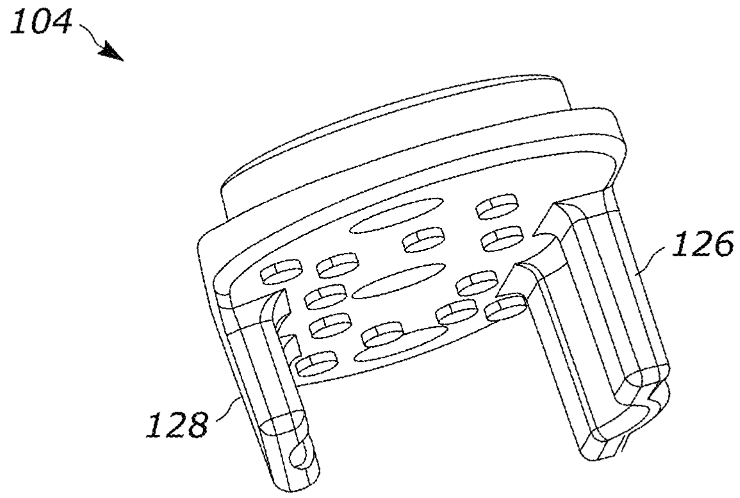
FIG. 16 is a perspective view of the right cap.

FIG. 16 is a perspective view of the right cap 104. FIG. 16 shows a difference in dimensions of the inner sidewall 128 (left side in FIG. 16) and the outer sidewall 126 (right side in FIG. 16). Specifically, in the example of FIG. 16, the depth dimension of the outer sidewall is larger than the depth dimension of the inner sidewall.

Figure 17:
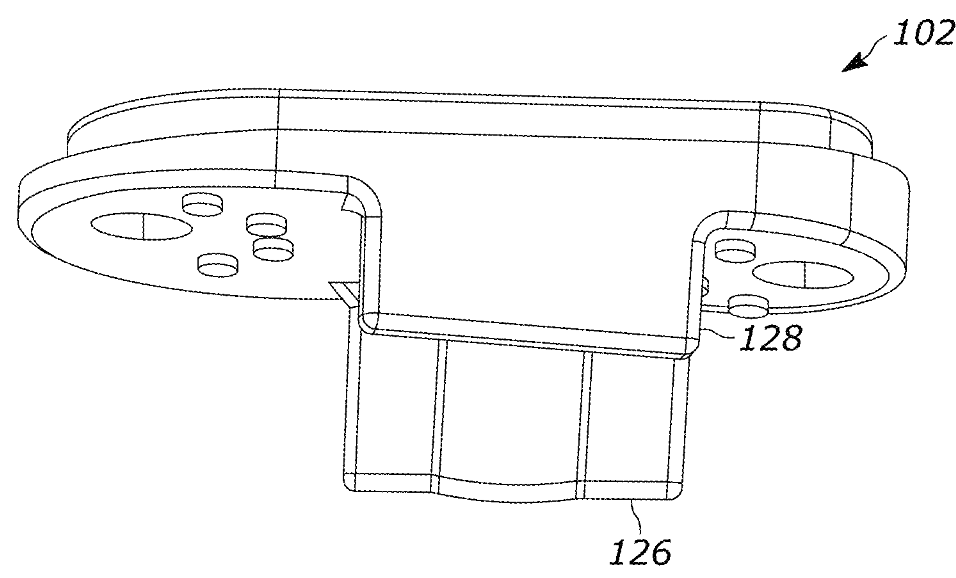
FIG. 17 is a side perspective view of the left cap showing the outer sidewall and the inner sidewall.

FIG. 17 is a side perspective view of the left cap showing the outer sidewall 126 and the inner sidewall 128.

Figure 18:
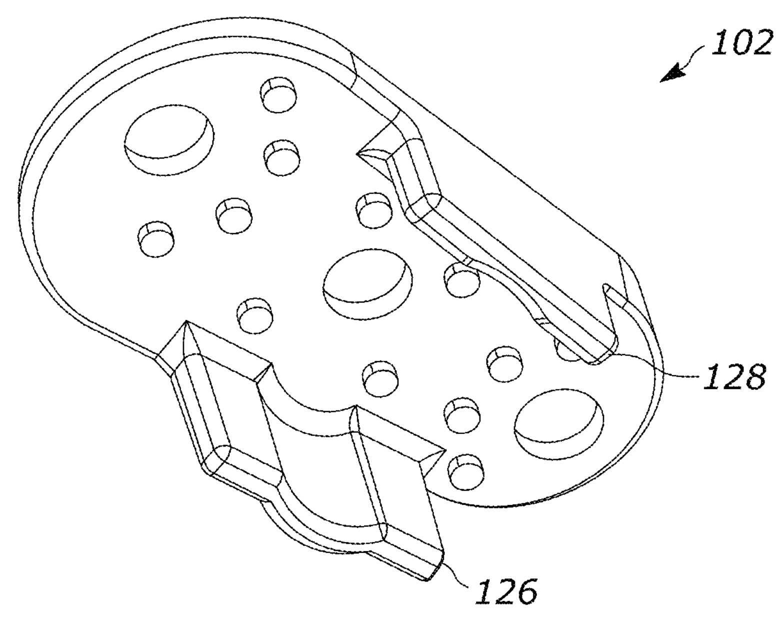
FIG. 18 is another perspective view of the left cap showing the outer sidewall and the inner sidewall.

FIG. 18 is another perspective view of the left cap 102 showing the outer sidewall 126 and the inner sidewall 128.

It should be understood that in an example, a left cap 102 would be a mirror image of a right cap 104 and a right cap would be a mirror image of a left cap.

Figure 19:
FIG. 19 is a front view of the intraoral appliance.
Figure 19:
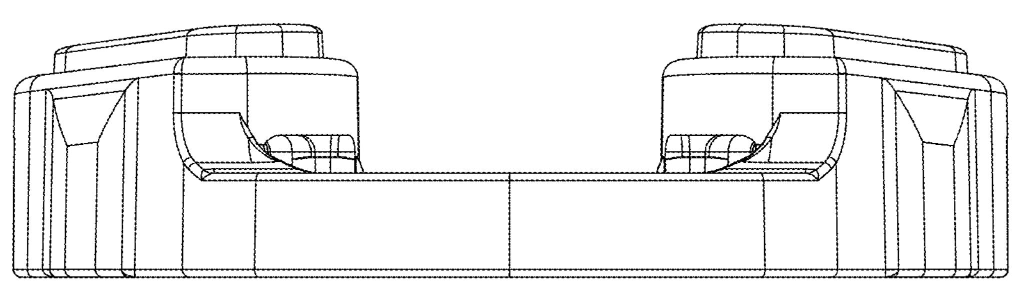

FIG. 19 is a front view of the intraoral appliance 100.

Figure 20:
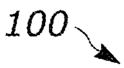
FIG. 20 is a back view of the intraoral appliance.
Figure 20:
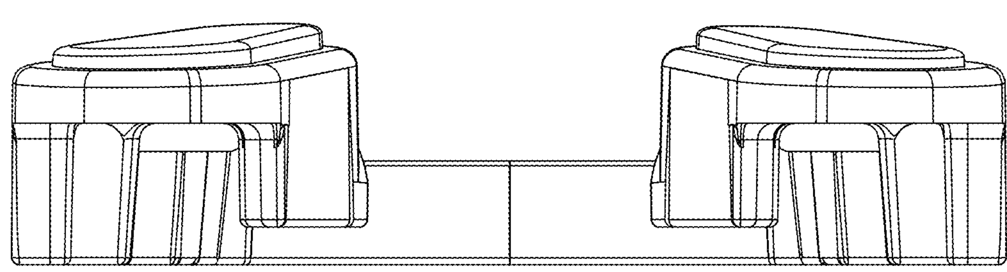

FIG. 20 is a back view of the intraoral appliance 100.

Figure 21:
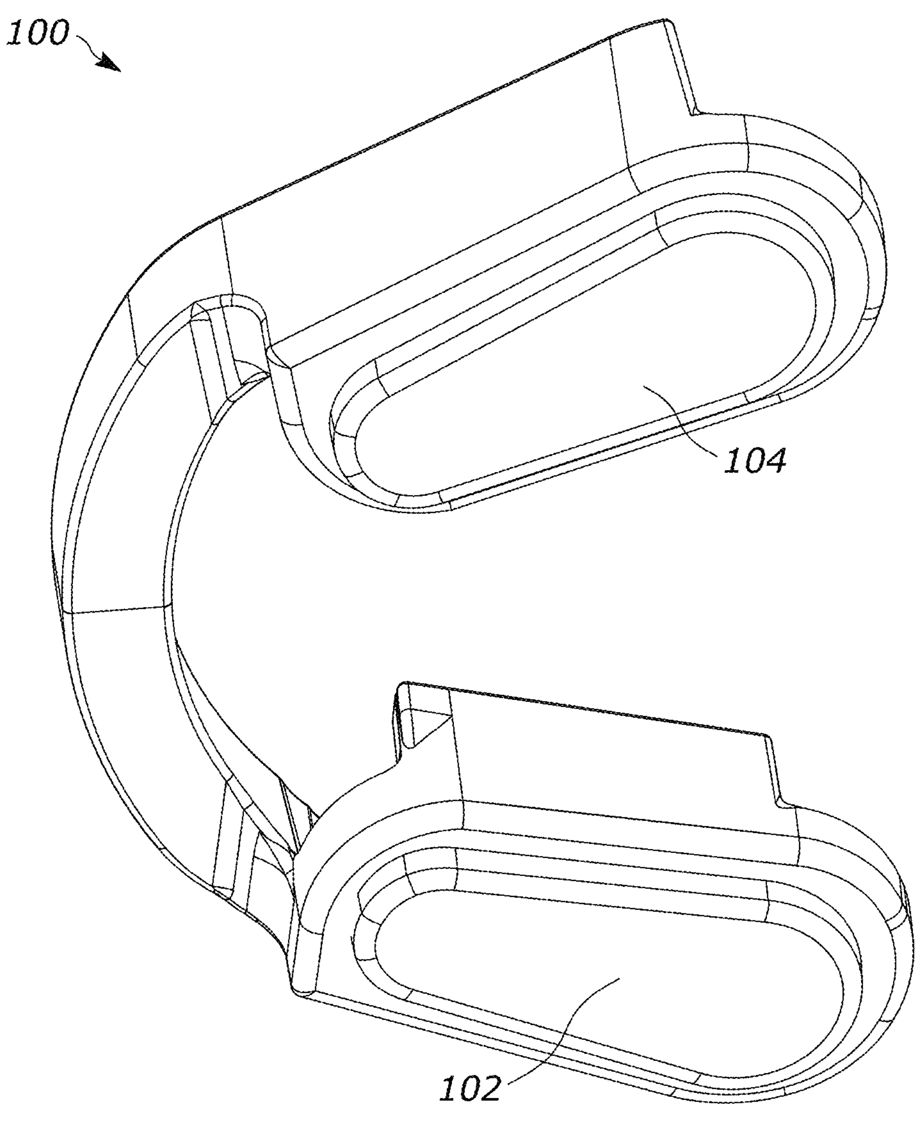
FIG. 21 is a perspective of the intraoral appliance that shows the exposed portion of the upper surface of the left cap and the exposed portion of the upper surface of the right cap.

FIG. 21 is a perspective of the intraoral appliance 100 that shows the exposed portion of the upper surface of the left cap 102 and the exposed portion of the upper surface of the right cap 104.

Figure 22:
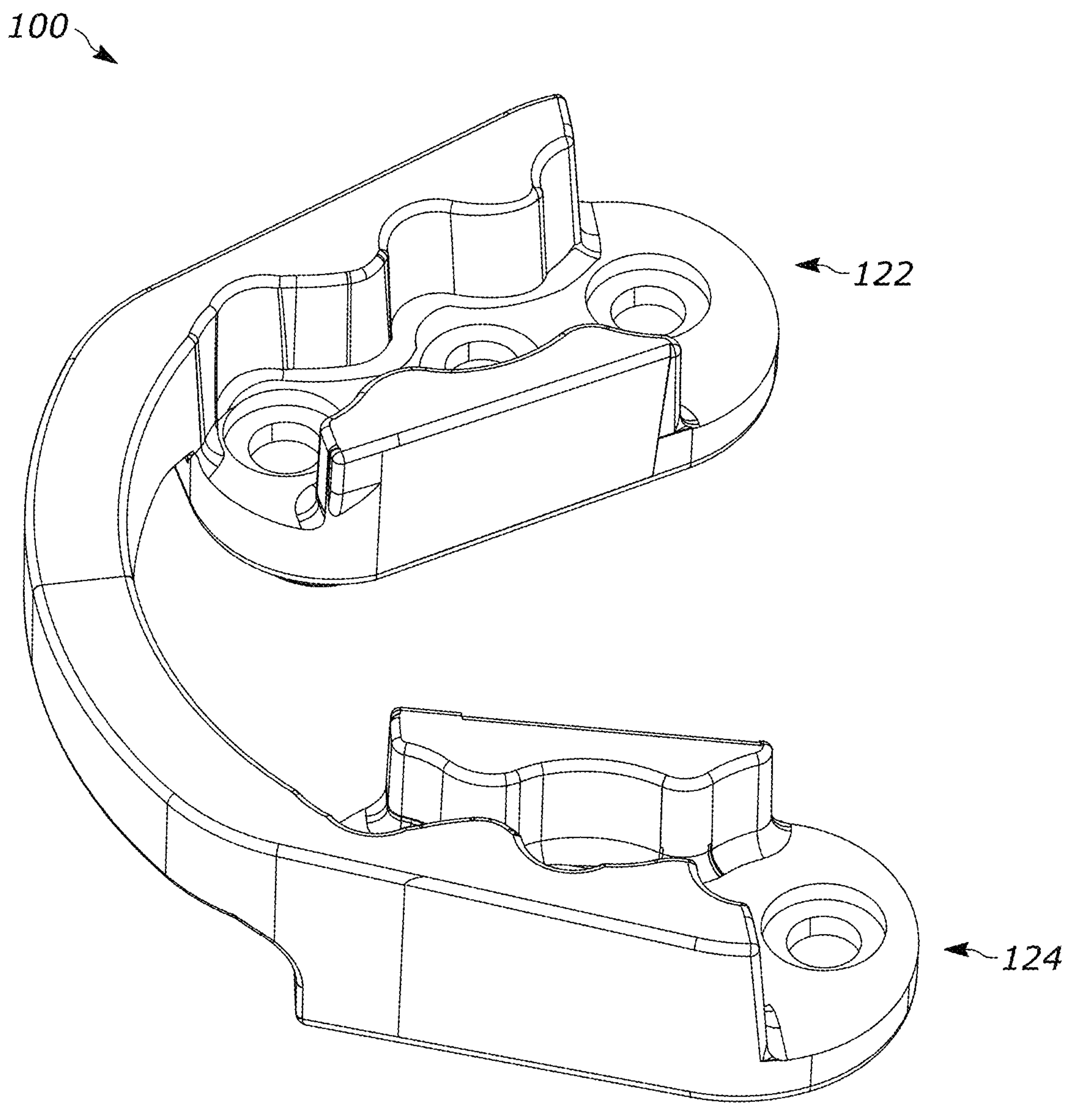
FIG. 22 is a perspective view of the intraoral appliance that shows the left-side teeth receiving channel and the right-side teeth receiving channel.

FIG. 22 is a perspective view of the intraoral appliance 100 that shows the left-side teeth receiving channel 122 and the right-side teeth receiving channel 124.

Figure 23:
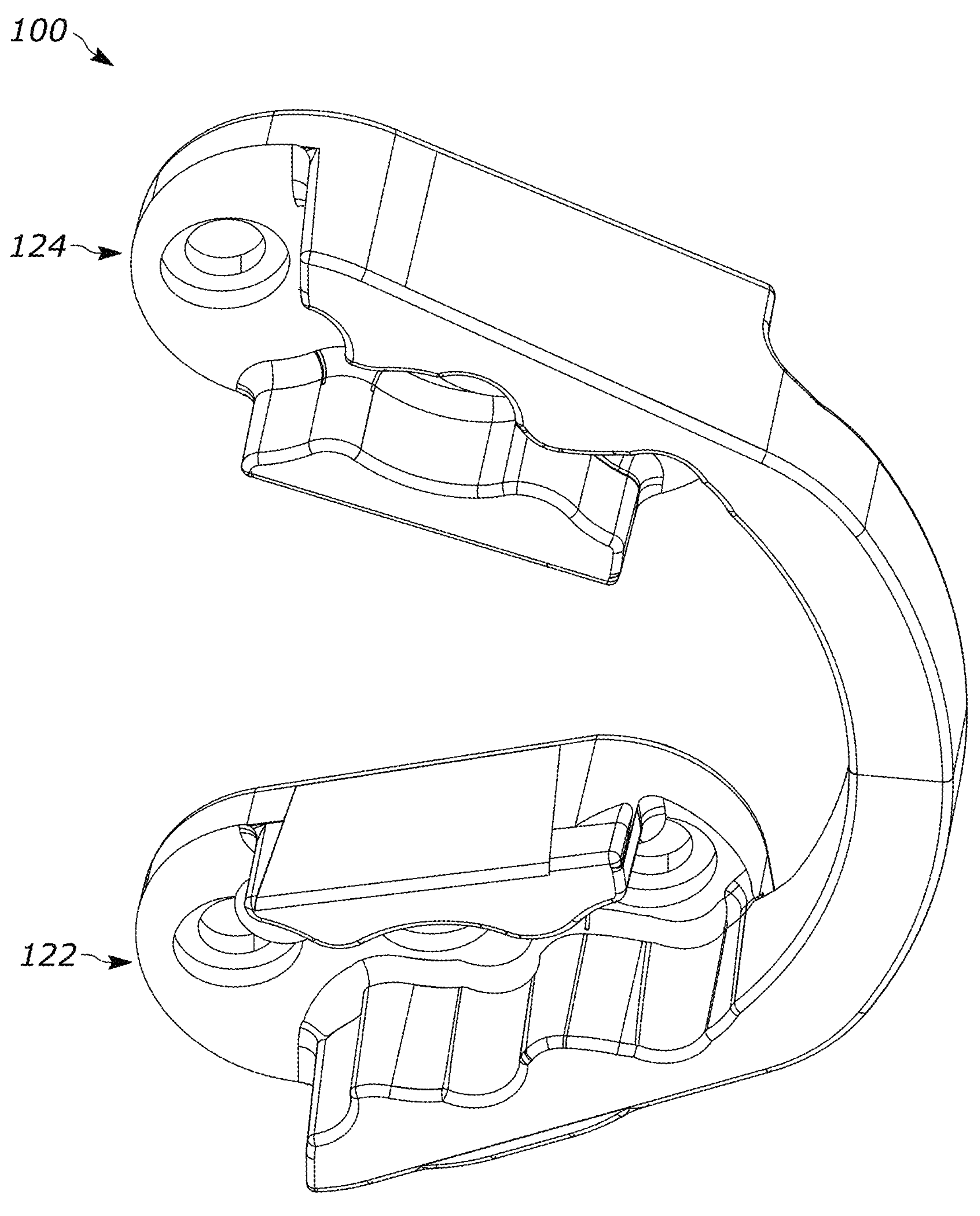
FIG. 23 is another perspective of the intraoral appliance that shows the left-side teeth receiving channel and the right-side teeth receiving channel.

FIG. 23 is another perspective of the intraoral appliance 100 that shows the left-side teeth receiving channel 122 and the right-side teeth receiving channel 124.

Although an example of an intraoral appliance is described above, variations of the intraoral appliance are expected. An example of another intraoral appliance is described with reference to FIGS. 24-28. The intraoral appliance includes the same novel design as is described above with a few subtle design variations, which are described herein.

Figure 24:
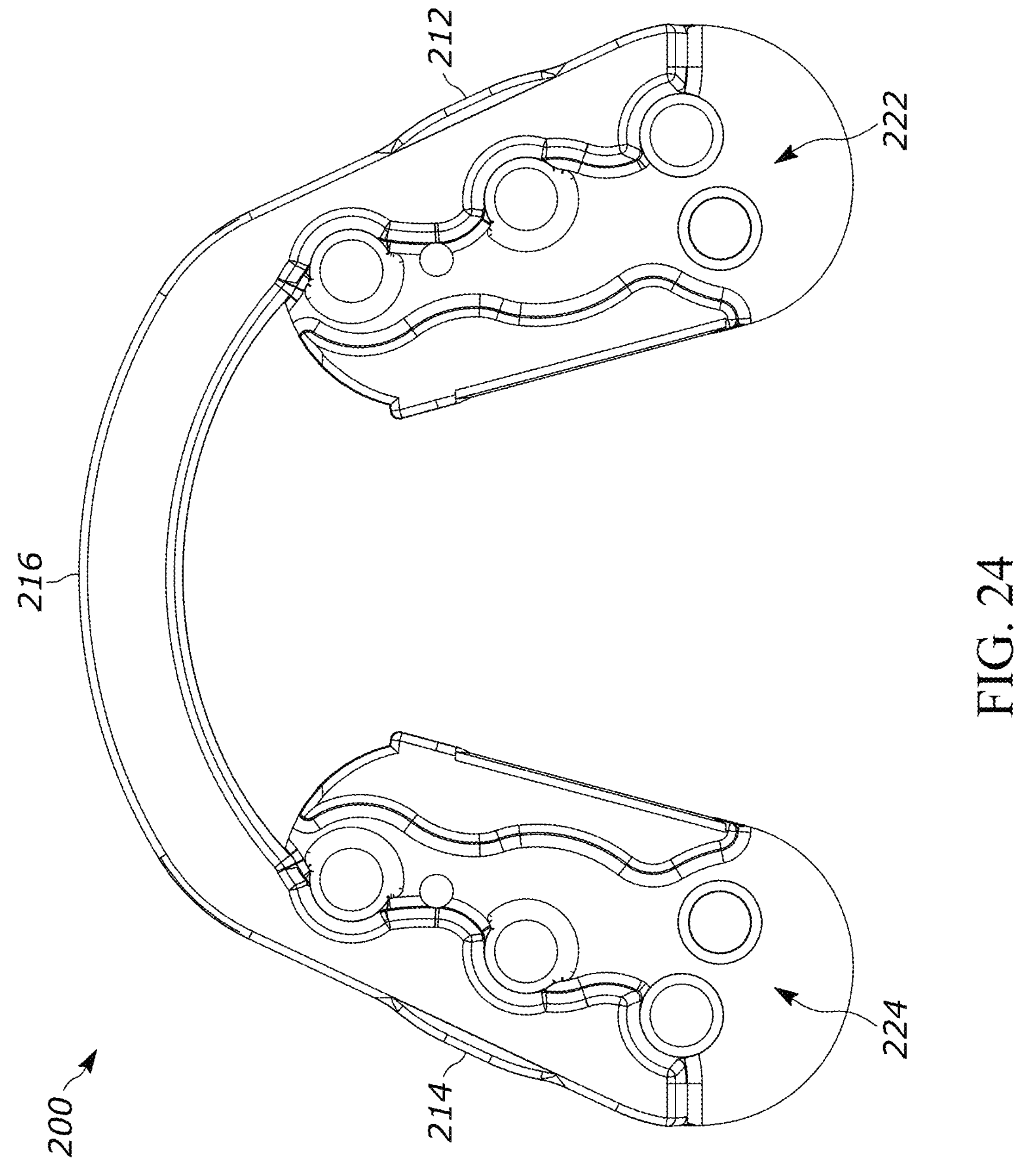
FIG. 24 is a bottom view of another intraoral appliance that includes a front band, a left cap casing, and a right cap casing.

FIG. 24 is a bottom view of an intraoral appliance 200 that includes a front band 216, a left cap casing 212, and a right cap casing 214. The left cap casing and the right cap casing form receiving channels that have a shape that is different from the receiving channels described above. In particular, the intraoral device includes a left-side receiving channel 222 and a right-side receiving channel 224 that have a slightly different shape from the corresponding left-side receiving channel 122 and right-side receiving channel 124 that are described above. For example, the receiving channels shown in FIG. 24 are more closed ended at the front end of the receiving channels. In some cases, the more closed front end of the receiving channels provides a better, more secure, fit over canine teeth.

Figure 25:
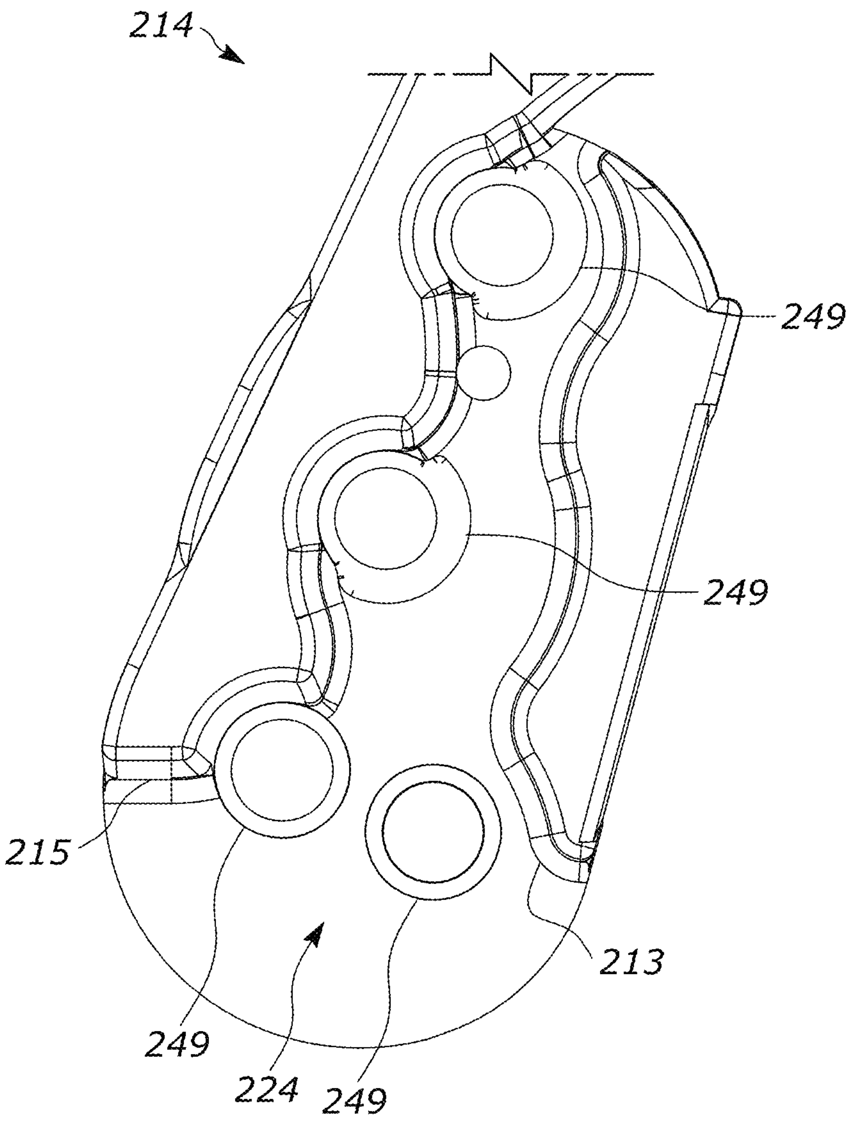
FIG. 25 is an expanded view of the right cap casing and the right-side receiving channel of the intraoral appliance of FIG. 24.

FIG. 25 is an expanded view of the right cap casing 214 and the right-side receiving channel 224, which is formed by the outer wall 215 and the inner side wall 213 that shows a more closed end at the front end of the receiving channel. The more closed end at the front end of the receiving channel provides for a better, more secure, fit over the right canine tooth. The example of FIG. 25 also includes openings 249 that are shifted a bit towards the outer side wall 215 and an additional opening 249 at the back end of the receiving channel. The three openings in a row are shifted towards the outer wall to better align with the location of teeth for a better fit and improved comfort. A similar design applies to the left cap casing 212.

Figure 26:
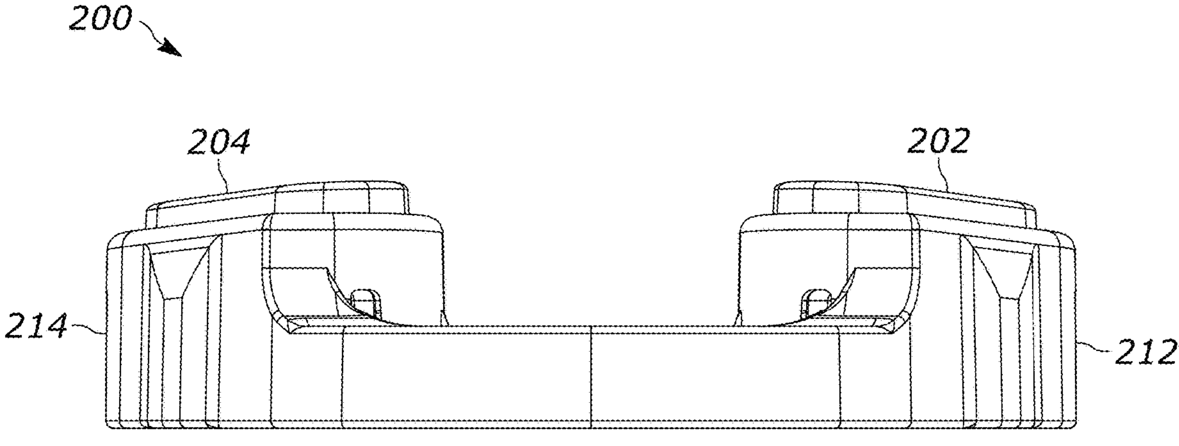
FIG. 26 is a front view of the intraoral appliance from FIG. 24 that shows design variations.

FIG. 26 is a front view of the intraoral appliance 200 that shows a couple of design variations. One design alternative is an increased distance between the top surface of the left cap 202 and the left cap casing 212 and an increased distance between the top surface of the right cap 204 and the right cap casing 214. Another design variation is a protruding portion of the overmolding that aligns with protrusions in the outer walls of the left and right caps. The protrusions in the overmolding help to maintain a desired thickness of the overmolding in and around the areas of corresponding protrusions in the outer walls of the caps, which may help improve the structural integrity of the intraoral appliance.

Figure 27:
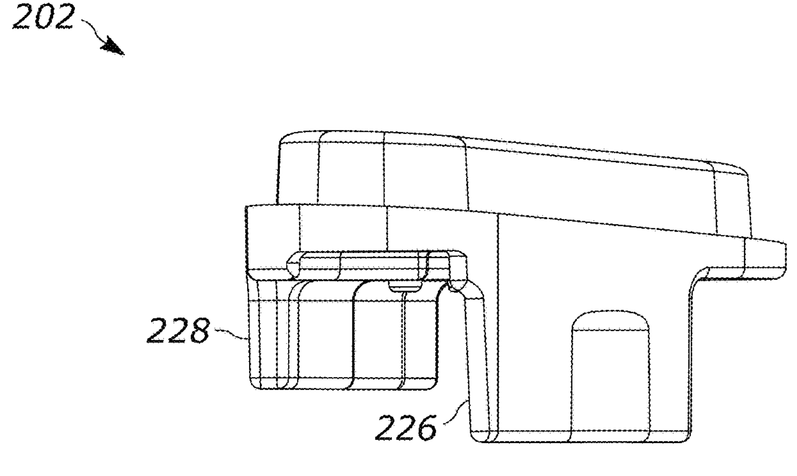
FIG. 27 is a perspective view of an example of the left cap for the intraoral appliance of FIG. 24.
Figures 28, 29:
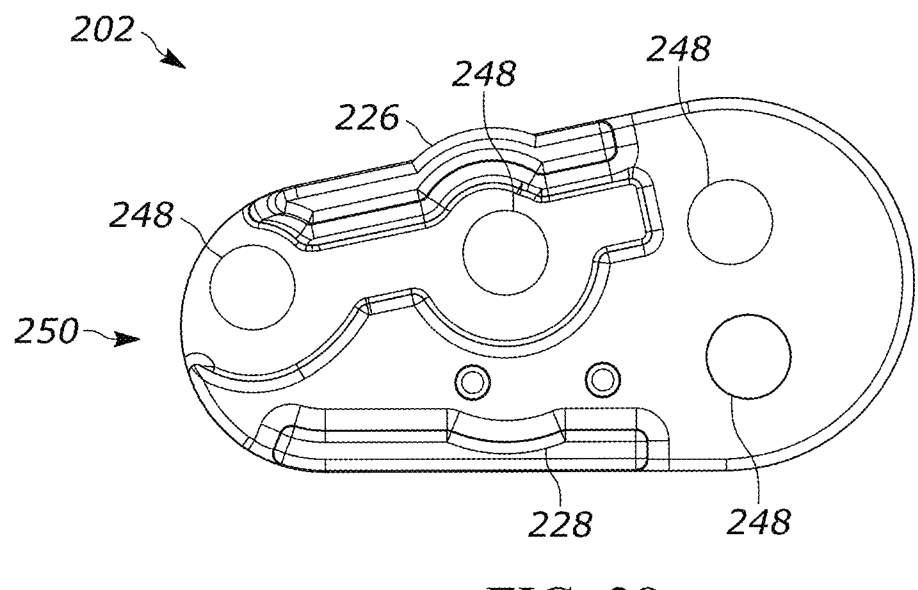
FIG. 28 is a bottom view of the left cap from FIG. 27.
FIG. 29 is a process flow diagram of an example of a process for producing an intraoral appliance that is similar to the intraoral appliance disclosed herein.

FIG. 27 is a perspective view of an example of the left cap 202 for the intraoral appliance 200. Design features of the left cap include an increased height between the upper surface of the cap and the body of the cap and increased height of the outer side wall 226 and of the inner side wall 228. The increased height between the upper surface of the cap and the body can help to make the desired slope to achieve the desired 7-10 mm opening. The increased height of the side walls can improve retention of the intraoral appliance onto the teeth, which can help with fit and comfort. The cap also includes a cutout section at the front end that corresponds to a cutout from a continuous channel in the cap, which is shown in FIG. 28. A similar design applies to the right cap 204.

FIG. 28 is a bottom view of the left cap 202 that shows the outer side wall 226, the inner side wall 228, pins 246, cavities 248, and a continuous channel 250. The cap includes an additional cavity 248 at the back end for additional support during overmolding, and the continuous channel 250 that allows silicon to flow out of the way of the teeth. The continuous channel extends to the front end of the cap and results in the cutout section that is visible in the perspective view of FIG. 27. The outer side wall 226 and the inner side wall 228 are also longer than the sidewalls 126 and 128 described above. The longer side walls and the increased height of the sidewalls provides a secure fit and good comfort. A similar design applies to the right cap 204. A similar design applies to the right cap 204.

An intraoral appliance is disclosed herein. In an example, an intraoral appliance includes a left cap, a right cap, and a body connected to the left cap and to the right cap. In the example, the left cap includes a bite plate having an upper surface and a lower surface, an inner sidewall extending from the lower surface, and an outer sidewall extending from the lower surface, wherein the inner sidewall and the outer sidewall form a left-side teeth receiving channel, the right cap includes a bite plate having an upper surface and a lower surface, an inner sidewall extending from the lower surface, and an outer sidewall extending from the lower surface, wherein the inner sidewall and the outer sidewall form a right-side teeth receiving channel, and the body includes a left cap casing, a right cap casing, and a front band between the left cap casing and the right cap casing. In the example, the left cap is secured within the left cap casing with a front end of the bite plate nearer to the front band than a back end of the bite plate, and wherein the upper surface and the lower surface of the bite plate form a wedge that slopes downward from the front end of the bite plate to the back end of the bite plate, and the right cap is secured within the right cap casing with a front end of the bite plate nearer to the front band than a back end of the bite plate, and wherein the upper surface and the lower surface of the bite plate form a wedge that slopes downward from the front end of the bite plate to the back end of the bite plate.

In an example, the outer sidewall of the left cap extends further from the lower surface of the bite plate than does the inner sidewall of the left cap, and the outer sidewall of the right cap extends further from the lower surface of the bite plate than does the inner sidewall of the right cap.

In an example, the inner sidewall and the outer sidewall of the left cap and the left cap casing form tooth-specific spaces configured to fit around at least two lower teeth, and the inner sidewall and the outer sidewall of the right cap and the right cap casing form tooth-specific spaces configured to fit around at least two lower teeth.

In an example, the left cap includes a stiffening structure at the intersection between the bite plate and the inner sidewall and a stiffening structure at the intersection between the bite plate and the outer sidewall, and the right cap includes a stiffening structure at the intersection between the bite plate and the inner sidewall and a stiffening structure at the intersection between the bite plate and the outer sidewall.

In an example, the slope of the wedges of the bite plates matches an angle measured from a fulcrum of the mandibular joint, which results in a 7-10 mm space between front teeth.

In an example, the body is formed from overmolded plastic material.

In an example, the body is formed from overmolded thermoplastic material in which the front band can stretch to fit to an arc of a jaw bone.

In an example, the left cap and the right cap are formed from a material with a Shore A grade hardness of 70-95.

In an example, the front band of the body is configured to go around the outside of lower teeth.

In an example, the front band of the body is configured to go around the outside of lower teeth between teeth and lips.

In an example, the left cap casing encases/covers the left cap except that a portion of the upper surface of the bite plate is exposed for direct contact with upper teeth, and the right cap casing encases/covers the right cap except that a portion of the upper surface of the bite plate is exposed for direct contact with upper teeth.

In an example, the front band is rectangular in shape, thickness of 2-10 mm, to enable adaptation of the length of the front band.

In an example, the bite plates of the left cap and the bite plate of the right cap are made a material having a Shore A grade hardness of 70-95 and the body is made of a thermoplastic.

In an example, the body is overmolded over the left cap and the right cap.

In an example, an intraoral appliance as disclosed herein is produced in a process that involves molding the caps, positioning the caps, and then overmolding the body around the caps. In one example, a method of manufacturing an intraoral appliance involves placing a left cap in a first position, placing a right cap in a second position, which is opposite the left cap, and forming a body, which includes forming a left cap casing around the left cap, forming a right cap casing around the right cap, and forming a front band between the left cap casing and the right cap casing. In an example, the positions of the left cap and the right cap correspond to positions of the caps as shown in, for example, FIGS. 2 and 13A-13C.

In an example, the body is formed by overmolding a thermoplastic material over the pre-positioned left cap and right cap. In an example, the left cap and the right cap are formed from a first material (e.g., a hard relative to the body) and the body is formed from a second material (e.g., a thermoplastic that is softer than the caps), wherein the first material and the second material are different materials.

FIG. 29 is a process flow diagram of an example of a process for producing/manufacturing an intraoral appliance that is similar to the intraoral appliance disclosed herein. At bock 2902, left and right caps are molded. At block 2904, the left and right caps are positioned, e.g., in positions that correspond to the desired positions of the caps relative to each other in a finished intraoral appliance. At block 2906, a body overmolded around the caps.

In one example, a method of manufacturing the intraoral appliance involves placing a left cap in a first position, placing a right cap in a second position, which is opposite the left cap, and forming a body, which includes forming a left cap casing around the left cap, forming a right cap casing around the right cap, and forming a front band between the left cap casing and the right cap casing. In an example, the left cap and the right cap are formed from a material having a Shore A grade hardness of 70-95 and the body is formed from a thermoplastic material that is softer than the material used to form the caps. In an example, the left cap and the right cap are placed in the first and second positions, respectively, based on measurement information from a user. For example, a user my use a custom smartphone application to obtain image and/or video information that can be used to custom size the caps and/or the body. In an example, the left cap includes a bite plate having an upper surface and a lower surface, an inner sidewall extending from the lower surface, and an outer sidewall extending from the lower surface, wherein the inner sidewall and the outer sidewall form a left-side teeth receiving channel, the right cap includes a bite plate having an upper surface and a lower surface, an inner sidewall extending from the lower surface, and an outer sidewall extending from the lower surface, wherein the inner sidewall and the outer sidewall form a right-side teeth receiving channel, wherein the left cap is secured within the left cap casing with a front end of the bite plate nearer to the front band than a back end of the bite plate, and wherein the upper surface and the lower surface of the bite plate form a wedge that slopes downward from the front end of the bite plate to the back end of the bite plate, and wherein the right cap is secured within the right cap casing with a front end of the bite plate nearer to the front band than a back end of the bite plate, and wherein the upper surface and the lower surface of the bite plate form a wedge that slopes downward from the front end of the bite plate to the back end of the bite plate. Although an example of a process for manufacturing an intraoral splint is described, other processes of manufacture may be used to produce an intraoral appliance as described herein.

Although the intraoral appliance is described herein as being worn on the lower teeth, the intraoral appliance could be designed to be worn on the upper teeth or both the lower teeth and upper teeth.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. An intraoral appliance comprising:

a left cap;

a right cap; and a body connected to the left cap and to the right cap;

the left cap including a bite plate having an upper surface and a lower surface, an inner sidewall extending from the lower surface, and an outer sidewall extending from the lower surface, wherein the inner sidewall and the outer sidewall form a left-side teeth receiving channel;

the right cap including a bite plate having an upper surface and a lower surface, an inner sidewall extending from the lower surface, and an outer sidewall extending from the lower surface, wherein the inner sidewall and the outer sidewall form a right-side teeth receiving channel;

the body including a left cap casing, a right cap casing, and a front band between the left cap casing and the right cap casing;

wherein the left cap is secured within the left cap casing with a front end of the bite plate nearer to the front band than a back end of the bite plate, and wherein the upper surface and the lower surface of the bite plate form a wedge that slopes downward from the front end of the bite plate to the back end of the bite plate;

wherein the right cap is secured within the right cap casing with a front end of the bite plate nearer to the front band than a back end of the bite plate, and wherein the upper surface and the lower surface of the bite plate form a wedge that slopes downward from the front end of the bite plate to the back end of the bite plate; and wherein the left cap casing encases the left cap except that a portion of the upper surface of the bite plate is exposed for direct contact with upper teeth, and wherein the right cap casing encases the right cap except that a portion of the upper surface of the bite plate is exposed for direct contact with upper teeth.

2. The intraoral appliance of claim 1, wherein:

the outer sidewall of the left cap extends further from the lower surface of the bite plate than does the inner sidewall of the left cap; and the outer sidewall of the right cap extends further from the lower surface of the bite plate than does the inner sidewall of the right cap.

3. The intraoral appliance of claim 1, wherein:

the inner sidewall and the outer sidewall of the left cap and the left cap casing form tooth-specific spaces configured to fit around at least two lower teeth; and the inner sidewall and the outer sidewall of the right cap and the right cap casing form tooth-specific spaces configured to fit around at least two lower teeth.

4. The intraoral appliance of claim 1, wherein:

the left cap includes a stiffening structure at the intersection between the bite plate and the inner sidewall and a stiffening structure at the intersection between the bite plate and the outer sidewall; and the right cap includes a stiffening structure at the intersection between the bite plate and the inner sidewall and a stiffening structure at the intersection between the bite plate and the outer sidewall.

5. The intraoral appliance of claim 1, wherein the slope of the wedges of the bite plates is configured to match an angle measured from a fulcrum of the mandibular joint, which results in a 7-10 mm space between front teeth.

6. The intraoral appliance of claim 1, wherein the body is formed from overmolded plastic material.

7. The intraoral appliance of claim 1, wherein the body is formed from overmolded thermoplastic material in which the front band can stretch to fit to an arc of a jaw bone.

8. The intraoral appliance of claim 1, wherein the left cap and the right cap are formed from a material with a Shore A grade hardness of 70-95.

9. The intraoral appliance of claim 1, wherein the front band of the body is configured to go around the outside of lower teeth.

10. The intraoral appliance of claim 1, wherein the front band of the body is configured to go around the outside of lower teeth between teeth and lips.

11. The intraoral appliance of claim 1, wherein the front band is rectangular in shape, thickness of 2-10 mm, to enable adaptation of the length of the front band.

12. The intraoral appliance of claim 1, wherein the bite plates of the left cap and the bite plate of the right cap are made a material having a Shore A grade hardness of 70-95 and the body is made of a thermoplastic.

13. The intraoral appliance of claim 1, wherein the body is overmolded over the left cap and the right cap.

* * * * *